(12) United States Patent
Silberg et al.

(10) Patent No.: US 8,236,491 B2
(45) Date of Patent: Aug. 7, 2012

(54) PROTEIN FRAGMENT COMPLEMENTATION ASSAY FOR THERMOPHILES

(75) Inventors: Jonathan Silberg, Houston, TX (US); Peter Q. Nguyen, Boston, MA (US)

(73) Assignee: William Marsh Rice University, Houston, TX (US)

( * ) Notice: Subject to any disclaimer, the term of this patent is extended or adjusted under 35 U.S.C. 154(b) by 45 days.

(21) Appl. No.: 12/889,157

(22) Filed: Sep. 23, 2010

(65) Prior Publication Data

US 2011/0287462 A1 Nov. 24, 2011

Related U.S. Application Data

(60) Provisional application No. 61/245,124, filed on Sep. 23, 2009.

(51) Int. Cl.
*C12Q 1/00* (2006.01)
*C12Q 1/48* (2006.01)

(52) U.S. Cl. ............... 435/4; 536/23.1; 536/23.2

(58) Field of Classification Search ............... None
See application file for complete search history.

(56) References Cited

OTHER PUBLICATIONS

Counago et al. Extremophiles (2005) 9, pp. 135-144.*
Nguyen et al. Protein Engin. Desig. Sele. (2008) 21, 303-310).*

* cited by examiner

*Primary Examiner* — Nashaat Nashed
(74) *Attorney, Agent, or Firm* — Boulware & Valoir

(57) ABSTRACT

A protein fragment complementation assay for thermophiles is provided wherein a thermophilic bacteria having a temperature-sensitive adenylate kinase is transformed with one or more vectors having sequences encoding a first test peptide operatively fused to a first portion of a thermostable adenylate and a second test peptide operatively fused to a second portion of the thermostable adenylate kinase. Association of the first and second test peptides allows association of the first and second portions of the thermostable adenylate kinase and growth of the thermophilic bacteria at a temperature greater than 70° C.

15 Claims, 9 Drawing Sheets

*adk$_T$*: original wild-type *adk* gene.
*adk$_G$*: an ortholog that encodes a protein that is not functional above 70°C *in vitro*.
*htk*: kanamycin nucleotidyltransferase to select cells grown on kanamycin-containing medium.
pTTA200-GsteAK(V): plasmid containing *adk$_G$*, *htk* genes for homologous recombination pWUR112: *E. Coli—T. Thermophilus* shuttle vector
pWUR112ΔEX: pWUR112 vector without the unique *ecoRI* and *xbaI* restriction sites
pJJS: pWUR112ΔEX with ampicillin resistance cassette (*bla*)
pJJS-Pro: pJJS with the *bla* gene replaced by a strong constitutive *slpA* promoter
pJJS-TnAK: pJJS-Pro with $adk_{Tn}$ gene after the second $P_{slpA}$ promoter

Additional Thermophilic Adenylate Kinases. These proteins have at least about 50% identity, and at least about 70% positives. Most have a gap of 1 or 2 residues, although at least one has a gap of 6 residues. Nonetheless, the alignments are quite clear suggesting that such proteins would also function in the invention. There are additional AK proteins in the same homology range that are not listed herein due to space considerations.

| SEQ ID NO. | Accession | Description | Identities / Positives |
|---|---|---|---|
| 6 | YP_001306220.1 | adenylate kinase [Thermosipho melanesiensis BI429] | 124/211 (58%) / 168/211 (79%) |
| 7 | YP_002335022.1 | adenylate kinase [Thermosipho africanus TCF52B] | 123/211 (58%) / 162/211 (76%) |
| 8 | YP_001410621.1 | adenylate kinase [Fervidobacterium nodosum Rt17-B1] | 117/216 (54%) / 162/216 (75%) |
| 9 | NP_069510.1 | adenylate kinase [Archaeoglobus fulgidus DSM 4304] | 129/211 (61%) / 157/211 (74%) |
| 10 | YP_003435538.1 | adenylate kinase [Ferroglobus placidus DSM 10642] | 119/211 (56%) / 153/211 (72%) |
| 11 | YP_001567816.1 | adenylate kinase [Petrotoga mobilis SJ95] | 117/216 (54%) / 155/216 (71%) |
| 12 | YP_001470238.1 | adenylate kinase [Thermotoga lettingae TMO] | 119/196 (58%) / 145/196 (73%) |
| 13 | YP_002250721.1 | adenylate kinase [Dictyoglomus thermophilum H-6-12] | 108/216 (50%) / 156/216 (72%) |
| 14 | ZP_02178348.1 | adenylate kinase [Hydrogenivirga sp. 128-5-R1-1] | 115/216 (53%) / 156/216 (72%) |
| 15 | YP_003401056.1 | adenylate kinase [Archaeoglobus profundus DSM 5631] | 115/199 (57%) / 146/199 (73%) |
| 16 | YP_002249627.1 | adenylate kinase [Thermodesulfovibrio yellowstonii DSM 11347] | 117/211 (55%) / 145/211 (68%) |
| 17 | YP_002352895.1 | adenylate kinase [Dictyoglomus turgidum DSM 6724] | 107/216 (49%) / 157/216 (72%) |
| 18 | NP_623811.1 | adenylate kinase [Thermoanaerobacter tengcongensis MB4] | 110/211 (52%) / 149/211 (70%) |
| 19 | YP_003677811.1 | adenylate kinase [Thermoanaerobacter mathranii subsp. mathranii str. A3] | 104/212 (49%) / 151/212 (71%) |
| 20 | YP_001040418.1 | adenylate kinase [Staphylothermus marinus F1] | 111/214 (51%) / 150/214 (70%) |
| 21 | YP_003477749.1 | adenylate kinase [Thermoanaerobacter italicus Ab9] | 102/212 (48%) / 150/212 (70%) |
| 22 | YP_003239198.1 | adenylate kinase [Ammonifex degensii KC4] | 107/211 (50%) / 147/211 (69%) |
| 23 | ZP_07677179.1 | adenylate kinase [Thermotogales bacterium mesG1.Ag.4.2] | 108/210 (51%) / 151/210 (71%) |
| 24 | ZP_07548510.1 | adenylate kinase [Thermoanaerobacter wiegelii Rt8.B1] | 104/212 (49%) / 147/212 (69%) |
| 25 | YP_003840733.1 | adenylate kinase [Thermincola sp. JR] | 105/211 (49%) / 151/211 (71%) |
| 26 | YP_003668434.1 | adenylate kinase [Staphylothermus hellenicus DSM 12710] | 108/204 (52%) / 143/204 (70%) |
| 27 | YP_001039315.1 | adenylate kinase [Clostridium thermocellum ATCC 27405] | 107/211 (50%) / 146/211 (69%) |
| 28 | YP_003317677.1 | adenylate kinase [Thermanaerovibrio acidaminovorans DSM 6589] | 104/204 (50%) / 141/204 (69%) |
| 29 | YP_001181036.1 | adenylate kinase [Caldicellulosiruptor saccharolyticus] | 105/212 (49%) / 148/212 (70%) |
| 30 | ZP_06255382.1 | adenylate kinase [Clostridium thermocellum JW20] | 106/211 (50%) / 145/211 (68%) |
| 31 | AAV31782.1 | adenylate kinase [Geobacillus stearothermophilus] | 102/212 (48%) / 151/212 (71%) | pJJS-Term: pJJS-Pro (in Fig. 3) with the *slpA* transcriptional terminator $T_{slpA}$.

PROTEIN FRAGMENT COMPLEMENTATION ASSAY FOR THERMOPHILES

PRIOR RELATED APPLICATIONS

The present invention claims priority to U.S. 61/245,124, entitled "Protein Fragment Complementation Assay for Thermophiles," filed on Sep. 23, 2009.

FEDERALLY SPONSORED RESEARCH STATEMENT

This invention was made with government support under Grant Number (NNX08A020G) awarded by National Aeronautic and Space Administration. The government has rights in the invention.

FIELD OF THE INVENTION

The invention relates to a protein fragment complementation assay for thermophilic organisms.

BACKGROUND OF THE INVENTION

Microbes that grow optimally above 60° C. (thermophiles) and 80° C. (hyperthermophiles) populate ecosystems where many biomolecules have reduced stability. To support cellular growth, proteins from such organisms have evolved distinct amino acid compositions and higher thermostability compared to orthologs found in mesophilic organisms that grow at lower temperatures. This latter feature has been exploited for a variety of biotechnological applications.

For example, thermostable DNA polymerases have revolutionized molecular biology, xylanases have made paper processing greener, and oligosaccharide-modifying enzymes have been harnessed for corn syrup production. There is also a great interest in harnessing thermotolerant microbes and their proteins for other industrial processes, such as biomass conversion to bioethanol or biohydrogen. However, no in vivo screens have been developed to help achieve these high-temperature metabolic engineering and synthetic biology goals.

A comparison of the findings from mesophile and hyperthermophile proteomic studies suggests that the lack of high-temperature protein-protein interactions screens may limit the discovery of useful protein complexes. A high-throughput screen for pairwise protein-protein interactions among almost one thousand *Pyrococcus horikoshii* proteins found only 56 hetero-interactions using a two-hybrid assay implemented at a temperature (37° C.) far below that of its optimal growth of 98° C.

This finding can be contrasted with similar screens for protein complexes in bacteria and yeast under near physiological conditions, which invariably find protein-protein interactions at a frequency that is more than an order of magnitude higher. The creation of an assay that can be used to assess protein complex formation at thermophile growth temperatures would have multiple advantages over available assays in studying natural and engineered proteins. High temperature assays are predicted to be superior at discovering interactions among proteins that require extreme temperatures to adopt their native conformation and among proteins whose interactions weaken as temperature is decreased from the levels where hyperthermophiles grow.

Using split adenylate kinases in protein fragment complementation has been discussed by Nguyen, et al in "Thermostability promotes the cooperative function of split adenylate kinases," published in *Protein Engineering, Design & Selection*, Vol. 21, pp. 303-310, 2008.

However, the system discussed in this paper was not in a high-temperature setting, and it is unclear whether the split fragments of adenylate kinases could still function or associate at high temperatures. Nor was the assay tested in a thermophilic organism. Therefore, there is a still need for a protein complementation assay capable of performing at high temperatures.

SUMMARY OF THE INVENTION

The use of the word "a" or "an" when used in conjunction with the term "comprising" in the claims or the specification means one or more than one, unless the context clearly dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

As used herein the term "thermophiles" is defined as microorganisms capable of surviving in an environment of temperatures higher than 50° C. "Hyperthermophiles" are an even more specialized form of thermophile, wherein such microorganisms are capable of surviving in a hyperthermal environment of temperatures greater than 70° C., and more preferably, 78° C. or more.

The term "temperature sensitive" means the activity of a protein decreases to at least 25%, and preferably 10%, of normal as the temperature increases to or beyond a thermophilic or hyperthermophilic temperature.

The term "thermostable" means that at least 50% activity, and preferably at least 60, 70, 75, or 80% of a protein's activity remains as the temperature increases to thermophilic temperatures.

When the adenylate kinase protein is described in terms of amino acid number, that number is to be ascertained by reference to SEQ ID NO. 1—in other words, the sequence in question is aligned with SEQ ID NO 1, e.g., using BLAST and the default parameters, and as shown in FIG. 7.

To establish an assay for studying protein complex formation within a living thermophile, *Thermotoga neapolitana* adenylate kinase ($AK_{Tn}$) was split into fragments that can be used as in a protein-fragment complementation assay (PCA) in *Thermus thermophilus*.

FIG. 1 illustrates the rationale of using split adenylate kinase fragments in a complementation assay. Specifically, a living cell that lacks a functional AK at the assay temperature (e.g., the cell has a temperature sensitive AK mutant) can be transformed with one or more expression vectors containing split AK proteins, each AK fragment fused to test proteins, that may or may not be binding pairs. Because adenylate kinase function is required for survival, where the test binding proteins do not associate, neither with the AK fragments associate, and the cell will not live.

On the other hand, if there is interaction between proteins to be tested, the two adenylate kinase fragments will be brought close enough together to also bind together and provide normal adenylate kinase function. Thus, the cell will survive, and hundreds of thousands of test proteins can easily be screened in this way.

$AK_{Tn}$ has many characteristics that make it suitable for designing a split enzyme that reports on protein-protein interactions at extreme temperatures. $AK_{Tn}$ is monomeric and extremely thermostable, exhibiting maximal phosphotransferase activity at 80° C. (ATP+AMP$\leftarrow\rightarrow$2ADP) and having a denaturing temperature of 99.7° C. Furthermore, $AK_{Tn}$ can be split to generate fragments that spontaneously associate and cooperatively function within a mesophilic bacterium growing at 40° C.

In an aspect of the present invention, there is provided a protein fragment complementation assay for thermophilic bacteria. The assay comprises: culturing a thermophilic bacteria having a temperature-sensitive adenylate kinase, a first vector having an expressable first test gene operatively fused to a first portion of a thermostable adenylate kinase gene encoding a first portion of a thermostable adenylate kinase, and a second vector having an expressable second test gene operatively fused to a second portion of the thermostable adenylate kinase gene encoding a second portion of the thermostable adenylate kinase. The first and second test genes encode first and second test peptides, and the association of the first and second test peptides allows association of the first and second portions of the thermostable adenylate kinase and growth of the thermophilic bacteria at a temperature greater than 70° C.

The first and second vector can be different or the same—in other words the vector can be polycistronic, coding for both test protein-AK fragment fusions, or the vector can contain two separate operons, each coding for one half of the system.

The adenylate kinase used in the present invention can come from any thermophilic bacteria, provided it has an adenylate kinase with at least about 50% protein identity to AAN86272 (SEQ ID NO: 1), and about 70% positive matches, preferably about 60% identity and about 75-80% positives matches and most preferably, at least 92% identity. Such adenylate kinases include but are not limited to the adenylate kinases from *Thermotoga neapolitana*, *Thermotoga maritime*, *Thermotoga naphthophila*, *Thermotoga petrophila*, or *Marinitoga piezophila*.

The adenylate kinase used in the present invention can be split to comprise: a. residues 1-79 or 80-220 from *Thermotoga neapolitana* (AAN86272) (SEQ ID NO: 1); b. residues 1-79 or 80-220 from *Thermotoga maritime* (NP_229279) (SEQ ID NO: 2); c. residues 1-79 or 80-220 from *Thermotoga naphthophila* (ZP_05471476) (SEQ ID NO: 3); d. residues 1-79 or 80-220 from *Thermotoga petrophila* (YP_001244903) (SEQ ID NO: 4); e. residues 2-80 or 81-220 from *Marinitoga piezophila* (ZP_05098624) (SEQ ID NO: 5) or combinations and homologs thereof.

Figure 7:
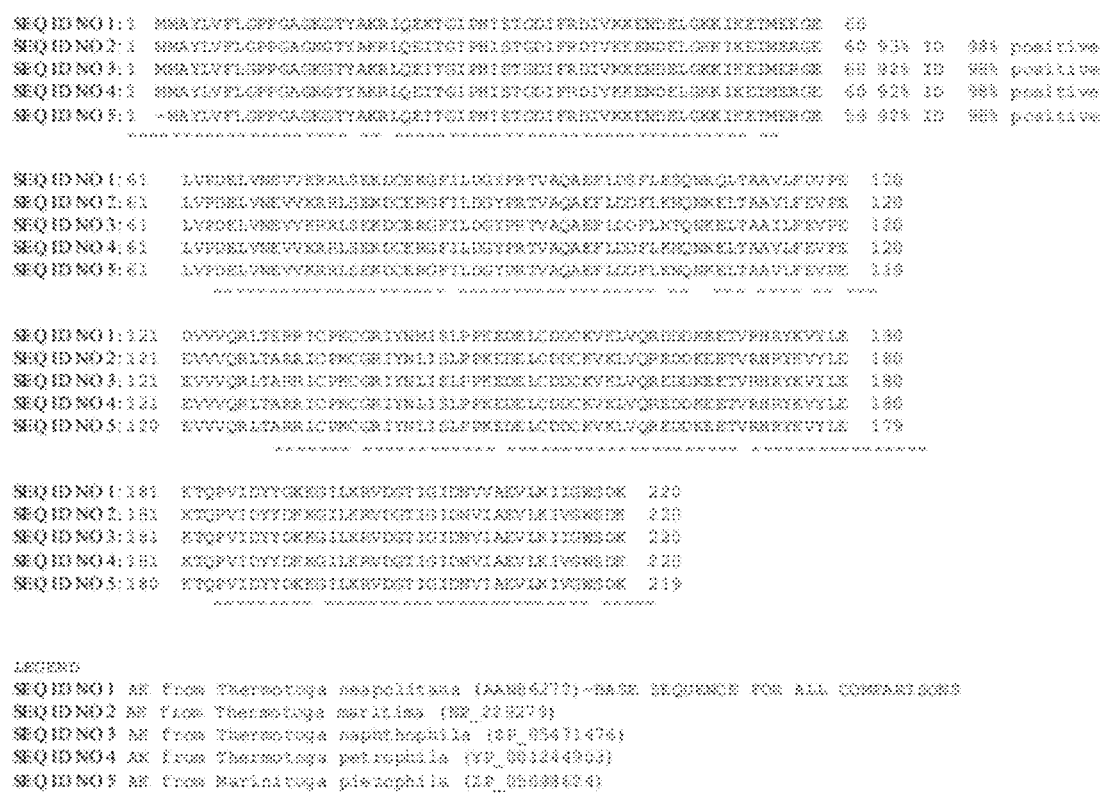

FIG. 7 shows a multi-alignment of the adenylate kinases from 5 thermophilic bacteria. As can be seen from the alignment, the adenylate kinase sequences from *Thermotoga maritima* (SEQ ID NO: 2), *Thermotoga naphthophila* (SEQ ID NO: 3), *Thermotoga petrophila* (SEQ ID NO: 4), and *Marinitoga piezophila* (SEQ ID NO: 5); have a 92% or higher identity to the AK sequence from *Thermotoga neapolitana* (SEQ ID NO: 1), indicating very high conservation of the adenylate kinase gene among thermophilic bacteria, and can thus be used in the protein complementary assay of the present invention.

FIG. 8 (SEQ ID NOS: 6-31) shows adenylate kinases from other bacteria that have at least 50% identity and at least about 70% positive matches that may also be used in the protein fragment complementation assay of the present invention.

In another aspect of the present invention, there is provided a kit for performing a protein complementation assay. The kit comprises a first expression vector encoding a first portion of a thermostable adenylate kinase and a second vector encoding a second portion of the thermostable adenylate kinase, wherein the first and second portions of the thermostable adenylate kinase are functional at temperatures higher than 60° C. when the first and second portions associate. Preferably, the vector contains suitable cloning sites for adding in the test protein sequences, and the test sequences can be added at either end of the AK fragments and be directly conjugated thereto, but are preferably separated from the adenylate kinase portion(s) by a short (5-15 amino acids) flexible linker sequence.

In a preferred embodiment, the first vector and the second vector are same vector, and the first and second portions of the thermostable adenylate kinase gene are contained in two operons, and more preferred the two portions are polycistronic on the vector with a cleavage site therebetween.

BRIEF DESCRIPTION OF THE DRAWINGS

FIG. 7 is an alignment comparison of adenylate kinases from *Thermotoga neapolitana*, *Thermotoga maritime*, *Thermotoga naphthophila*, *Thermotoga petrophila*, and *Marinitoga piezophila* (SEQ ID NOS: 1-5 respectively).

FIG. 8 is a table listing adenylate kinases from other bacteria that have at least about 50% identity and at least about 70% positives. (SEQ ID NOS: 6-31)

DESCRIPTION OF EMBODIMENTS OF THE INVENTION

Figure 1:
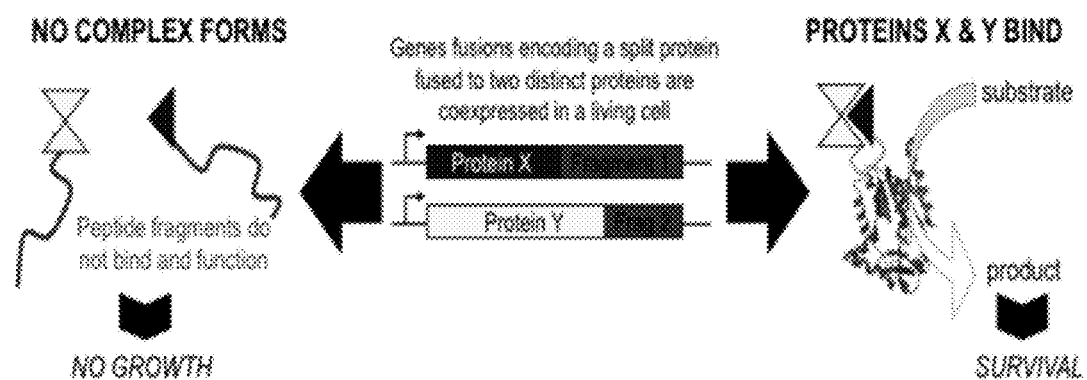
FIG. 1 illustrates the rationale of a protein fragment complementation assay.

The following examples are illustrative only, and are not intended to unduly limit the scope of the invention.

Example 1

Materials

Agar was from DIFCO,™ Gelrite was from RESEARCH PRODUCTS INTERNATIONAL,™ and all other bacterial growth media components were from BD BIOSCIENCES™ and SIGMA-ALDRICH.™

Quikchange™ mutagenesis reactions were performed using PFUTURBO™ DNA polymerase from STRATAGENE,™ genes were amplified for cloning using VENT$_R$™ DNA Polymerase from NEW ENGLAND BIOLABS,™ and restriction endonucleases were obtained from ROCHE BIOCHEMICAL,™ NEW ENGLAND BIOLABS,™ and PROMEGA.™

Synthetic oligonucleotides were from OPERON BIOTECHNOLOGY,™ pET™ vectors were from EMD BIOSCIENCES,™ *Escherichia coli* XL1-BLUE™ cells used for plasmid amplification and cloning were from STRATAGENE,™ and kits for DNA purification were from ZYMO RESEARCH™ and QIAGEN.™

Example 2

Methods

*Thermus thermophilus* HB8 (ATCC #27634) was used as the parent strain for adk gene replacement. Liquid growth was performed in Evian-Thermus Medium (EvTM), which contains 8 g tryptone, 4 g yeast extract, and 3 g NaCl per liter of Evian mineral water. EvTM-agar plates containing 3% agar were used for growth at temperatures below 75° C., whereas EvTM-Gelrite plates containing 1.5% Gelrite were used for growth at higher temperatures to minimize desiccation.

Electrocompetent HB8 cells were prepared using a protocol similar to that previously described (de Grado, et al. 1999). Cells (500 mL) were grown to mid-logarithmic phase in EvTM medium ($A_{600} \approx 0.7$) at 65° C., concentrated by centrifugation at 5,000 rpm for 30 min, washed with 10% glycerol (250 mL) two times at room temperature, resuspended in 10% glycerol (2 mL), and frozen at −80° C. in aliquots (100 µL).

Transformations were performed by mixing 3 µg of vector (100-800 µg/µL) and 100 µL of electrocompetent cells, incubating the mixture on ice for one hour, and electroporating the cells with a pulse of 12.5 kV/cm in 0.1 cm cuvettes using a BIORAD™ MICROPULSER.™ Cells were immediately transferred to EvTM medium (5 mL) that had been prewarmed to 60° C. and incubated for 4 hrs at 60° C. in a 50 mL flask shaking at 150 rpm.

Cells transformed with pJJS-derived expression vectors (100 µL) were plated onto EvTM-agar plates containing 15 µg/mL bleocin (CALBIOCHEM™) and incubated at 65° C. for 72 hours. Cells transformed with the adk gene replacement vectors were plated onto EvTM-agar plates containing 250 µg/mL kanamycin and incubated at 60° C. for 72 hours, and colonies identified as inviable at 80° C. (e.g. the native AK gene was replaced with a temperature sensitive mutant AK), were cured of their plasmid by restreaking them twice onto EvTM-agar plates lacking antibiotic at 60° C.

Desiccation was minimized during incubation by placing agar plates into ZIPLOC™ bags, removing extra air from the bags, and sealing all but one inch of the bag. To avoid condensation on plates during incubation, freshly poured plates were incubated with the agar facing up at 37° C. for 1-2 hours prior to use.

Figure 2:
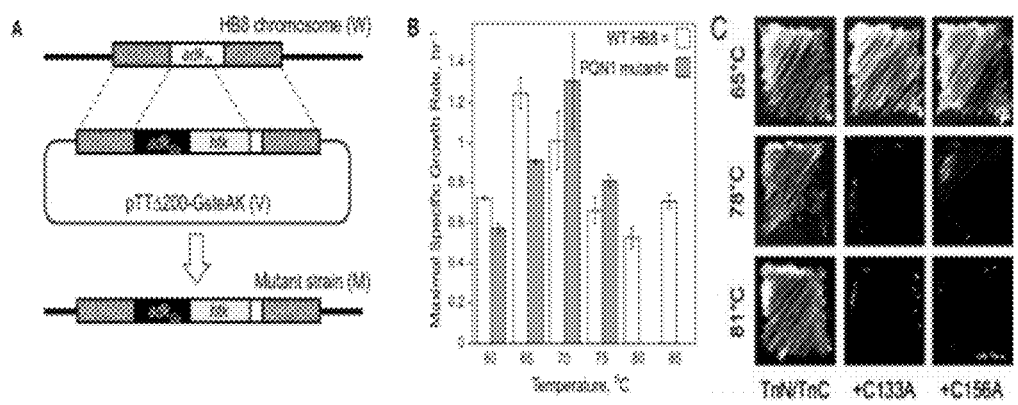
FIGS. 2A-2C illustrate the creation of PQN1 mutant strain from *Thermus thermophilus* HB8, the growth rate measurement of the wild type HB8 and mutant PQN1 strains, and the result of growth complementation by different fragments of adenylate kinase.

FIG. 2 illustrates how the vector used for adk gene replacement was built. A 1,600 bp segment of *T. thermophilus* HB8 genomic DNA including approximately 1,000 bp adjacent to the adk start codon, the adk gene, and 45 bp after the adk stop codon was PCR amplified from genomic DNA and cloned into pUC18 using hindIII and xbaI. In addition, approximately 1,000 bp of genomic DNA including the last 121 bp of the adk gene and sequence adjacent to the adk stop codon was PCR amplified from genomic DNA using and cloned into the pUC18-derived vector containing the first amplicon using xbaI and ecoRI to create pTT1.

The gene encoding a highly thermostable kanamycin nucleotidyltransferase (htk) (Hoseki, et al. 1999) with only a RBS was PCR amplified from pMK-18 (de Grado, et al. 1999) and cloned into pTT1 using xbaI to obtain pTT2. This plasmid was modified by two QUIKCHANGE™ mutagenesis reactions to create pTT2-BK, a plasmid that has a unique bmtI site 8 bp prior to the adk start codon and a kpnI site 147 bp before the adk stop codon.

The adk gene from *Geobacillus stearothermophilus* (adk$_{Gs}$) was PCR amplified from genomic DNA and cloned into pTT2-BK using bmtI and kpnI to obtain pTT-GsteAK. Selection of HB8 transformed with pTT-GsteAK on EvTM-agar plates containing 250 µg/mL kanamycin yielded multiple colonies. After curing these strains of their plasmid by sequentially streaking them onto two EvTM-agar plates lacking antibiotic, PCR amplification with primers complementary to the HB8 adk gene revealed that the native adk had not been removed from the chromosome (data not shown), suggesting that the small amount of genomic DNA separating the adk and htk genes in pTT-GsteAK had facilitated off-pathway recombination. To remove this DNA, the htk resistance cassette was PCR amplified and cloned into the kpnI and xbaI sites in pTT-GsteAK to create pTTΔ200-GsteAK, which was the vector successfully used for gene replacement, as shown in FIG. 2A.

Cultures of HB8 and PQN1 cells grown overnight at 60° C. in EvTM were used to inoculate 50 mL flasks of prewarmed EvTM. Cells were grown over a range of temperatures (60 to 85° C.), and the optical density at 600 nm was measured to acquire growth curves until the stationary phase. Each data trace was fit in Kaleidagraph to a modified Gompertz equation, $\ln(N/N_0) = A^* (\exp(-\exp((\mu_m^*(2.71828183)/A)^*(\lambda - t) + 1)))$, where N is the population size as determined by $A_{600}$ measurements, $N_0$ is the initial $A_{600}$ upon inoculation, A is the asymptotic value of the curve, $\lambda$ is the lag period, and $\mu_m$ is the maximum specific growth rate. For each strain and temperature, we report the mean and standard error for the maximum specific growth rate calculated from three independent measurements, as shown in FIG. 2B.

Figure 3:
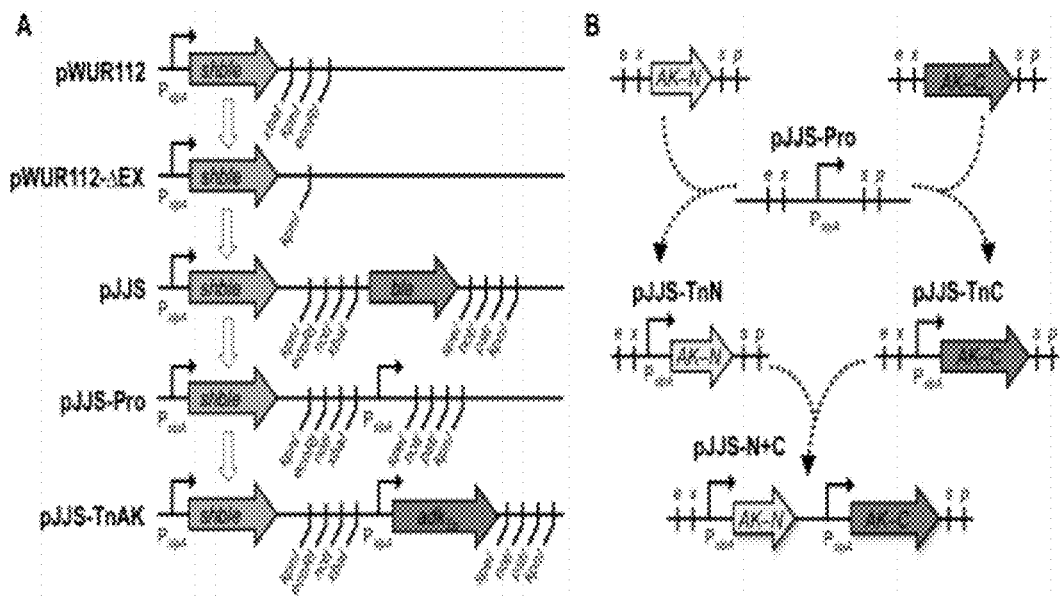
FIGS. 3A-3B illustrate the design and creation of vectors encoding different adenylate kinase fragments.

The *E. coli*-*T. thermophilus* shuttle vector pWUR112 (Brouns, et al. 2005) containing a thermostable bleomycin selectable marker (shble) was modified through QuikChange mutagenesis to remove the unique ecoRI and xbaI restriction sties and create pWUR112-ΔEX, as shown in FIG. 3A. An ampicillin resistance cassette (bla) PCR amplified with primers that incorporated flanking kpnI-ecoRI-notI-xbaI and speI-notI-pstI-kpnI sites was cloned into the kpnI site of pWUR112-ΔEX to create pJJS. The strong constitutive slpA promoter (Faraldo, et al. 1992) was PCR amplified from genomic DNA and subcloned into pJJS using xbaI and pstI, replacing the bla gene, to create pJJS-Pro, as shown in FIG. 3A. In addition, the slpA transcriptional terminator $T_{slpA}$ (Faraldo, et al. 1992) was PCR amplified from *T. thermophilus* HB8 genomic DNA using primers that incorporate flanking ecoRI-notI-xbaI and speI-notI-pstI sites, digested with ecoRI and pstI, and cloned into pJJS digested with ecoRI and pstI to yield pJJS-Term. The pJJS, pJJS-Pro, and pJJS-Term vectors are all compatible with a modular subcloning assembly strategy, which was used for construction of the majority of protein expression vectors.

The *Thermotoga neapolitana* adk gene was PCR amplified from pET21d-TnAK (Vieille, et al. 2003) using primers that incorporate flanking ecoRI-notI-xbaI and speI-notI-pstI restriction sites, digested with xbaI and pstI, and cloned into pJJS-Pro that had been digested with speI and pstI to create pJJS-TnAK. In addition, fragments of the *T. neapolitana* adk gene that encode residues 1-79 (TnN) and 80-220 (TnC) were PCR amplified from pET21d-TnN and pET24d-TnC (Nguyen, et al. 2008), respectively, using primers that incorporate flanking ecoRI-notI-xbaI and speI-notI-pstI restriction sites and cloned into pJJS-Pro using a similar protocol to create pJJS-TnN and pJJS-TnC, respectively, as shown in FIG. 3B.

A vector for coexpressing TnN and TnC, pJJS-N+C, was created by digesting pJJS-TnC with xbaI and pstI, and subcloning the excised gene into pJJS-TnN that had been digested with speI and pstI. QuikChange mutagenesis was used to modify pJJS-TnC to create vectors that express TnC with C133A (pJJS-TnC133) and C156A (pJJS-TnC156) mutations. These plasmids were then used to create the coexpression vectors pJJS-N+C133 and pJJS-N+C156, using a cloning scheme similar to that described for pJJS-N+C.

Figure 9:
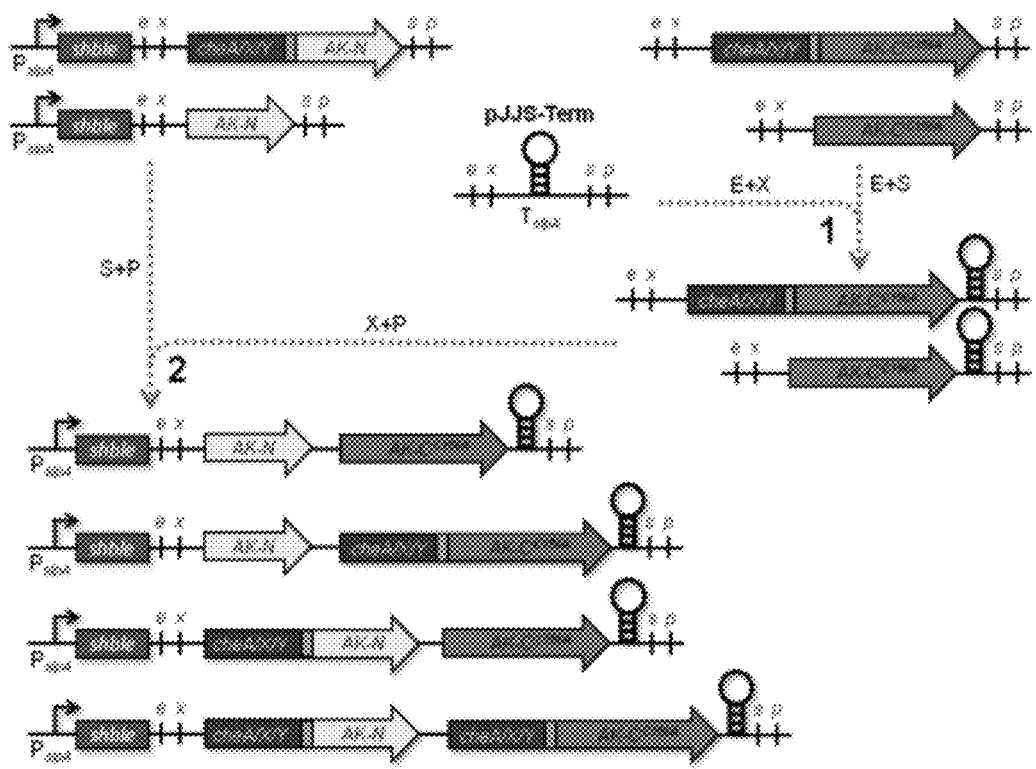
FIG. 9 shows the strategy used to create vectors that express AK fragment fusions from a single polycistronic transcript.

The strategy used to create vectors that express AK fragment fusions from a single polycistronic transcript is shown in FIG. 9. The genes encoding the P1 and P2 domains of CheA (CheA$^{P1P2}$; residues 1-264), full-length CheX, and full-length CheY were PCR amplified from *Thermotoga maritima* MSB8 genomic DNA (ATTC #43589D-5), and pJJS-Pro vectors were generated that encode each of these genes fused in frame to the N-terminus of TnN and TnC$^{C156A}$ mutation through a linker that is predicted to be flexible (GASGGGSSGGHM)) (SEQ ID NO: 32).

These gene fusions were PCR amplified using primers that incorporate ecoRI-notI-xbaI sites upstream of the ribosomal binding site (RBS) and speI-notI-pstI restriction sites adjacent to the stop codon. The RBS in the amplified gene fusions is identical in sequence to that found adjacent to the *T. thermophilus* HB8 slpA promoter (Faraldo, et al. 1992), and it includes twenty nucleotides upstream of the annotated RBS.

PCR amplified gene fusions encoding the TnN fragments were cloned into pJJS, whereas the gene fusions encoding TnC$^{C156A}$ were cloned into pJJS-Term. Upon sequence verification, the rbs-cheA/X/Y-tnC$^{C156A}$-T$_{slpA}$ gene fusions were excised from their vectors using XbaI and PstI and subcloned into the vectors harboring the rbs-cheA/X/Y-tnN gene fusions that had been digested with SpeI and PstI. Table 1 lists all vector intermediates, and Table 2 lists the vectors used for complementation analysis.

TABLE 2

Vectors used for complementation studies in *T. thermophilus* PQN1

| Name | Proteins expressed | Expression |
| --- | --- | --- |
| pJJS-TnAK | AK$_{Tn}$ | monocistronic |
| pJJS-N + C | TnN & TnC | monocistronic |
| pJJS-N + C133 | TnN & TnC$^{C133A}$ | monocistronic |
| pJJS-N + C156 | TnN & TnC$^{C156A}$ | monocistronic |
| pJJS-N + C156-poly | TnN & TnC$^{C156A}$ | polycistronic |
| pJJS-YN + AC156 | CheY-TnN & CheA$^{P1P2}$-TnC$^{C156A}$ | polycistronic |
| pJJS-YN + XC156 | CheY-TnN & CheX-TnC$^{C156A}$ | polycistronic |
| pJJS-YN + YC156 | CheY-TnN & CheY-TnC$^{C156A}$ | polycistronic |
| pJJS-YN + C156 | CheY-TnN & TnC$^{C156A}$ | polycistronic |
| pJJS-N + AC156 | TnN & CheA$^{P1P2}$-TnC$^{C156A}$ | polycistronic |
| pJJS-XN + XC156 | CheX-TnN & CheX-TnC$^{C156A}$ | polycistronic |
| pJJS-N + XC156 | TnN & CheX-TnC$^{C156A}$ | polycistronic |
| pJJS-XN + C156 | CheX-TnN & TnC$^{C156A}$ | polycistronic |
| pJJS-XN + AC156 | CheX-TnN & CheA$^{P1P2}$-TnC$^{C156A}$ | polycistronic |

Complementation analysis involving monocistronic constructs was assessed by streaking colonies obtained from transformations on solid medium in glass petri dishes, and incubating these plates at temperatures ($\geq$78° C.) where PQN1 cannot grow like parental HB8 because it has a temperature sensitive adenylate kinase. Complementation studies involving the polycistronic constructs were performed by spotting a defined titer of cells grown at 65° C. onto EvTM-Gelrite plates, and evaluating growth after 24 hours at 78° C. In the spotting experiments, 5 mL EvTM liquid cultures containing 5 µg/mL bleocin were inoculated with colonies obtained from transformations and cultured overnight at 65° C. while shaking at 150 rpm.

The optical density of each culture was measured after 24 hours, and each culture was diluted to an A$_{600}$ of 0.5, pelleted by centrifugation, and resuspended in 25% glycerol so that it was concentrated 4 fold. Serial dilutions (1×, 10×, 100×, and 1000×) of the resuspended cells (10 µL each) were spotted onto EvTM-Gelrite plates. After incubation at 78° C. for 24 hours, growth at each spot was analyzed using a Fluor Chem 5500 imager (Alpha-Innotech), and the program ImageJ was used to quantify the relative growth of spots.

TABLE 1

Plasmids derived from pJJS that were used to construct protein expression vectors. The protein coding region cloned into pJJS is indicated as well as the regulatory elements cloned adjacent to that region

| Name | 5' DNA | Protein coding region | 3' DNA |
| --- | --- | --- | --- |
| pJJS | — | — | — |
| pJJS-Pro | P$_{slpA}$-RBS | — | — |
| pJJS-Term | — | — | T$_{slpA}$ |
| pJJS-TnN | P$_{slpA}$-RBS | TnN | — |
| pJJS-TnC | P$_{slpA}$-RBS | TnC | — |
| pJJS-TnC133 | P$_{slpA}$-RBS | TnC$^{C133A}$ | — |
| pJJS-TnC156 | P$_{slpA}$-RBS | TnC$^{C156A}$ | — |
| pJJS-AN | P$_{slpA}$-RBS | CheA$^{P1P2}$-GASGGGSSGGHM-TnN | — |
| pJJS-XN | P$_{slpA}$-RBS | CheX-GASGGGSSGGHM-TnN | — |
| pJJS-YN | P$_{slpA}$-RBS | CheY-GASGGGSSGGHM-TnN | — |
| pJJS-AC156 | P$_{slpA}$-RBS | CheA$^{P1P2}$-GASGGGSSGGHM-TnC$^{C156A}$ | — |
| pJJS-XC156 | P$_{slpA}$-RBS | CheX-GASGGGSSGGHM-TnC$^{C156A}$ | — |
| pJJS-YC156 | P$_{slpA}$-RBS | CheY-GASGGGSSGGHM-TnC$^{C156A}$ | — |
| pJJS-rbsTnC156-T$_{slpA}$ | RBS | TnC$^{C156A}$ | T$_{slpA}$ |
| pJJS-rbsAC156-T$_{slpA}$ | RBS | CheA$^{P1P2}$-GASGGGSSGGHM-TnC$^{C156A}$ | T$_{slpA}$ |
| pJJS-rbsXC156-T$_{slpA}$ | RBS | CheX-GASGGGSSGGHM-TnC$^{C156A}$ | T$_{slpA}$ |
| pJJS-rbsYC156-T$_{slpA}$ | RBS | CheY-GASGGGSSGGHM-TnC$^{C156A}$ | T$_{slpA}$ |
| pJJS-rbsTnN | RBS | TnN | — |
| pJJS-rbsAN | RBS | CheA$^{P1P2}$-GASGGGSSGGHM-TnN | — |
| pJJS-rbsXN | RBS | CheX-GASGGGSSGGHM-TnN | — |
| pJJS-rbsYN | RBS | CheY-GASGGGSSGGHM-TnN | — |

In order to test our system we chose to use various chemotaxis proteins that are known to self assemble in vivo. *T. maritima* MSB8 CheA$^{P1P2}$, CheX, and CheY were overexpressed in *E. coli* Rosetta cells (NOVAGEN™) using plasmids kindly provided by the Crane lab (Park, et al. 2004, Park, et al. 2004) that express these proteins with N-terminal (His)$_6$ tags. Cells transformed with these plasmids were grown at 37° C. in LB supplemented with 25 µg/mL kanamycin, protein expression was induced at an A$_{600}$ of ~0.5 bp adding 1 mM isopropylthio-β-D-galactoside (IPTG), cells were harvested by centrifugation after 3 hours of growth, and cells were lysed by resuspending them in PSI buffer (50 mM phosphate pH 7.5, 150 mM NaCl, 10 mM imidazole) containing 1 mM MgCl$_2$, 300 µg/mL lysozyme, and 2 U/mL DNase I.

Cells were frozen at −80° C., thawed, and centrifuged at 15k×g for 1 hr. Cleared lysate was filtered through a sterile 0.2 micron syringe filter, applied to a 2 mL nickel talon affinity column (Qiagen) equilibrated with PSI buffer, washed with 10 column volumes of PSI buffer, and bound protein was eluted using PSI containing 250 mM imidazole. The elution containing CheA$^{P1P2}$ (theoretical pI=4.6) was diluted 100 fold into 50 mM phosphate pH 7.5 buffer, applied to a 5 mL HiTrap-Q HP anion exchange column (GE Healthcare), and eluted using a linear gradient from 0 to 500 mM NaCl in 50 mM phosphate pH 7.5. All purified proteins were dialyzed overnight into PS buffer (50 mM phosphate pH 7.5 and 150 mM NaCl), and stored at −80° C.

An ÄKTA FPLC was used for all protein purification. Protein concentrations were determined by measuring their absorbance with a Cary 50 spectrophotometer, using the calculated extinction coefficients $\epsilon_{280}$(CheA$^{P1P2}$)=5,120 M$^{-1}$cm$^{-1}$ and $\epsilon_{280}$(CheY)=2,560 M$^{-1}$cm$^{-1}$, as calculated from the primary sequence by the PEPSTATS algorithm. Dynamic light scattering was performed with a Malvern Instruments Zetasizer Nano ZS using samples that contained 115 µM of each protein in PS buffer (50 mM Phosphate pH 7.5 and 150 mM NaCl). These samples were analyzed in triplicate at 78° C. using a 1 cm quartz cuvette at a backscattering angle of 173° after a 5 minute incubation at 78° C. Data processing was performed using the high resolution analysis model provided with Zetasizer software v6.01.

To generate a *Thermus thermophilus* HB8 mutant for evaluating AK fragment complementation above 75° C., homologous recombination was used to replace its adk gene with adk$_{Gs}$, an ortholog that encodes a protein that is not functional above 70° C. in vitro (Bae and Phillips 2004). Gene replacement was performed by transforming HB8 cells with the pTTΔ200-GsteAK plasmid and selecting for growth at 60° C. on EvTM-agar plates containing kanamycin as previously described (Cameron, et al. 2004). Since HB8 cells cannot replicate this plasmid, they are only able to grow if the htk gene is integrated into the chromosome as illustrated in FIG. 2A.

Kanamycin-resistant colonies were screened for growth at 80° C. in EvTM-liquid culture, and strains identified as nonviable at this temperature were cured of their plasmid. PCR analysis of genomic DNA from one of the strains obtained (designated PQN1) confirmed integration of adk$_{Gs}$ into the targeted chromosome, and DNA sequencing of these amplicons revealed that PQN1 expresses an AK$_{Gs}$ with an E70V mutation.

To better characterize the temperature-sensitive phenotype of PQN1, we compared its specific maximal growth rate in liquid medium to the parental strain used for recombination. FIG. 2B shows that *T. thermophilus* HB8 grows over a broad temperature range (60 to 85° C.), as was previously known. In contrast, PQN1 only displayed detectable growth up to 75° C., ten degrees lower than the maximal growth temperature of the parental HB8 strain. We also investigated the effect of temperature on the growth of PQN1 on solid medium over a range of temperatures. As in liquid medium, PQN1 did not grow above 75° C. under these conditions. However, this temperature-sensitive phenotype could be rescued by transformation with a vector (pJJS-TnAK) that constitutively expresses the hyperthermophilic AK$_{Tn}$ using the strong constitutive slpA promoter (Faraldo, et al. 1992).

Example 3

Results

To be useful as a protein complementation assay, fragments of a split protein must exhibit impaired function in the absence of protein tags (test proteins fused thereto). Otherwise, the split AK fragments would self associate, even without the fusion proteins, and this would add to background noise and decrease sensitivity There are two ways to address this problem—one being to encode with the test proteins a selectable marker, and the second to modify the AK fragments so that they are less active without the test proteins fused to them.

To evaluate whether the AK fragments self associate at 78° C. without a test protein fused thereto (as observed with homologous fragments of *B. subtilis* AK at 40° C.), we evaluated the growth of PQN1 transformed with pJJS-N+C, a vector that constitutively coexpresses monocistronic transcripts encoding each fragment. FIG. 2C shows that PQN1 growth was complemented by TnN and TnC above 75° C. without the assistance of protein tags that drive their association.

We next examined whether point mutations within the tetracysteine motif that coordinates zinc abrogate the association and cooperative function of TnC and TnN sufficiently to allow them to be used as a more effective protein complementation assay in PQN1. These cysteines were targeted for mutagenesis since previous studies have shown zinc binding by the tetracysteine motif in the LID domain enhances AK thermostability.

We found that coexpression of adenylate kinase TnN with TnC fragments harboring either a Cys133Ala (TnC$^{C156A}$) or Cys156Ala (TnC$^{C156A}$) mutation could not complement PQN1 growth at 78° C. This suggests that disruption of zinc binding in the TnC$^{C133A}$ and TnC$^{C156A}$ polypeptides causes a decrease in the association of TnC with TnN and/or a decrease in the thermostability of AK$_{Tn}$-fragment complexes, as observed previously upon loss of zinc from full-length AK$_{Tn}$.

To test whether adenylate kinase TnN and TnC$^{C156A}$ can be used with PQN1 to report on protein-protein interactions, we examined whether PQN1 growth could be complemented at 78° C. by vectors that express these polypeptides fused to different combinations of the *Thermotoga maritima* MSB8 chemotaxis proteins (CheA$^{P1P2}$, CheX, and CheY). These proteins were chosen because biochemical and biophysical studies have provided evidence for interactions between CheA$^{P1P2}$ and CheY (Park, et al. 2004), CheX and CheY (Park, et al. 2004), and CheX and CheX (Park, et al. 2004). Among these pairwise interactions, only the CheA$^{P1P2}$ and CheY interaction has been studied at a temperature where thermophiles grow, although the maximum temperature where this interaction has previously been analyzed (70° C.) is lower than the minimum temperature (78° C.) where our assay was performed (Park, et al. 2004).

Figure 4:
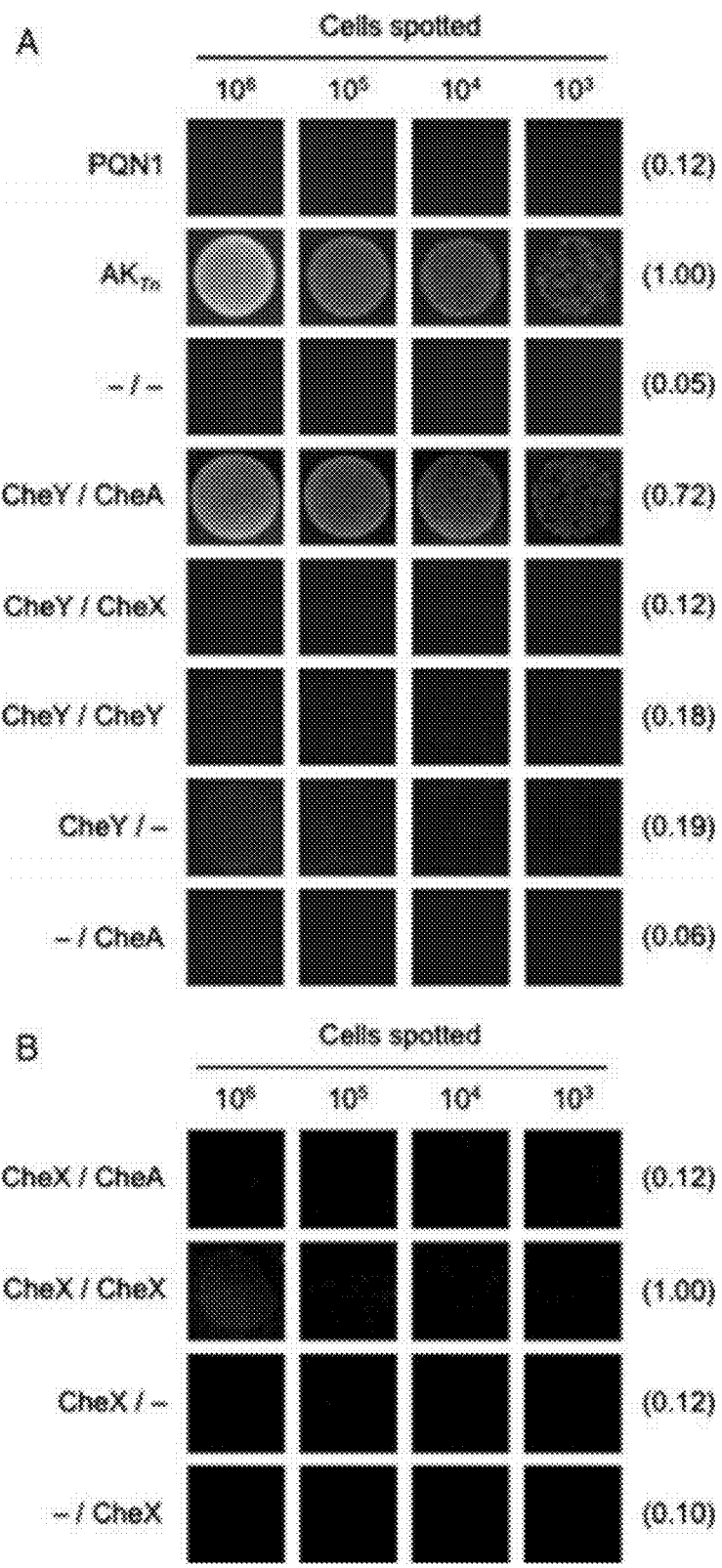
FIGS. 4A-4B illustrate the detection of chemotaxis protein-protein interaction.

FIG. 4A compares the growth of untransformed PQN1 with cells harboring vectors that coexpress TnN and TnC$^{C156A}$ fused to different combinations of chemotaxis proteins via a twelve amino acid linker. For these experiments, both adenylate kinase TnN and TnC$^{C156A}$ fragments were expressed from a single polycistronic transcript with the thermostable bleomycin selectable marker.

We found that PQN1 coexpressing CheY-TnN and CheA$^{P1P2}$-TnC$^{C156A}$ grew after 24 hours of incubation at 78° C. at all titers analyzed, similar to that observed with PQN1 harboring a vector that expresses full-length AK$_{Tn}$. The average magnitude of the growth was calculated for the highest titers analyzed in each experiment by integrating the intensity of replicate spots using ImageJ.

This analysis revealed that PQN1 coexpressing CheY-TnN and CheA$^{P1P2}$-TnC$^{C156A}$ grows 72% as dense as cells expressing full-length AK$_{Tn}$. In contrast, the growth detected with PQN1 expressing AK fragments fused to only CheY (CheY-TnN and TnC$^{C156A}$) or CheA$^{P1P2}$ (TnN and CheA$^{P1P2}$-TnC$^{C156A}$) is ≧4-fold lower than that of cells expressing AK fragments fused to CheY and CheA$^{P1P2}$ at the highest titer and undetectable at the lowest titer analyzed. Similarly, little growth was observed after 24 hours with PQN1 transformed with vectors that express TnN and TnC$^{C156A}$ fused to nothing, CheY and CheX, and CheY and CheY.

Taken together, these findings provide direct evidence that the complementation observed with PQN1 coexpressing CheY-TnN and CheA$^{P1P2}$-TnC$^{C156A}$ arises because the association of these chemotaxis proteins drives the cooperative function of the AK$_{Tn}$ fragments at the physiological growth temperatures of *T. maritima* as predicted. CheY and CheX are also predicted to interact in *T. maritima*. However, the lack of growth with CheY and CheX protein fusions is consistent with studies which find that CheY must be phosphorylated to associate strongly with CheX.

Since CheX is a dimer in its crystal structure, we also investigated whether two CheX molecules could enhance AK$_{Tn}$-fragment complementation of PQN1 at 78° C. like CheA$^{P1P2}$ and CheY. FIG. 4B shows that PQN1 cells coexpressing CheX-TnN and CheX-TnC$^{C156A}$ display detectable growth after a 24 hour incubation at 78° C. At the highest titer analyzed, this growth is ≧5.5-fold higher than that of PQN1 cells harboring vectors that only express one of the two AK$_{Tn}$ fragments as a fusion with CheX, i.e., CheX-TnN and TnC$^{C156A}$ or TnN and CheX-TnC$^{C156A}$.

In addition, PQN1 cells coexpressing CheX-TnN and CheX-TnC$^{C156A}$ grow to a density that is ~8-fold higher than that of cells expressing CheX-TnN and CheA$^{P1P2}$-TnC$^{C156A}$ chemotaxis protein fusions that are not expected to interact and promote AK-fragment function. However, PQN1 were not complemented by CheX-TnN and CheX-TnC$^{C156A}$ to the same extent as with CheY-TnN and CheA$^{P1P2}$-TnC$^{C156A}$. Growth was only observed with cells expressing CheX protein fusions at the highest titer of cells analyzed even after incubation for an additional day, whereas growth could be detected with CheA$^{P1P2}$ and CheY protein fusions at all titers analyzed after 24 hours.

Figure 5:
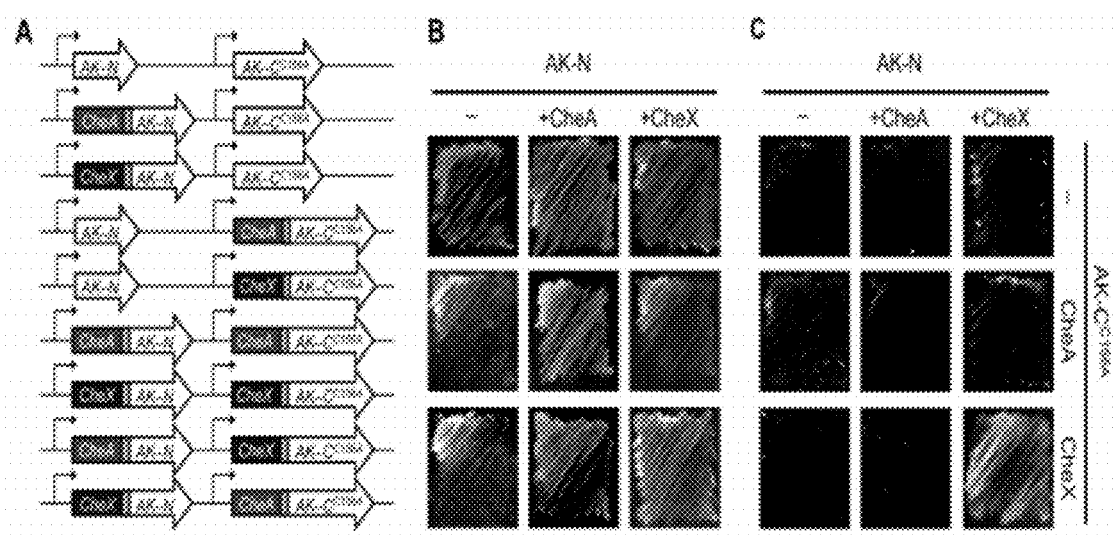
FIGS. 5A-5C illustrate the constructs of different combinations of adenylate kinase fragments and CheA/CheX genes and the results of complementation assay.

To examine if the split AK$_{Tn}$ harboring the C156A mutation can report on protein-protein interactions in a living thermophile, we next created vectors for expressing each fragment fused to the *Thermotoga maritia* chemotaxis proteins CheA, CheX, and CheY using a protocol similar what is mentioned above and assessed their ability to complement PQN1 growth defects. Structural studies have shown that CheX homodimerizes and CheA and CheY form a stable complex, suggesting that AK complementation of PQN1 should be enhanced through fusion to these proteins. FIGS. 5A-5C show the results from complementation studies examining pairwise interactions between CheA and CheX. PQN1 growth defects at 78° C. were complemented when the N- and C-terminal adenylate kinase fragments were both fused to CheX as predicted.

To confirm that this enhanced complementation arose because of CheX dimerization, we also examined whether the split AK$_{Tn}$ could complement the growth of PQN1 when only one of the fragments was fused to CheX (e.g., coexpressing AK-N and CheX::AK-C$^{C156A}$). As shown in FIGS. 5A-5C, PQN1 harboring plasmids that express all combinations of the AK-N and AK-C$^{C156A}$ fragments fused to CheA, CheX, or no protein were streaked on EvTM-Gelrite plates and incubated at 65° C. (FIG. 5B) and 78° C. (FIG. 5C) for 48 hrs. These experiments revealed that CheX only assists in AK fragment complementation when both polypeptide fragments are fused to CheX. Consistent with previous studies that suggest CheA and CheX do not interact, AK fragments fused to CheA and CheX (or CheA and CheA) could not complement PQN1.

Figure 6:
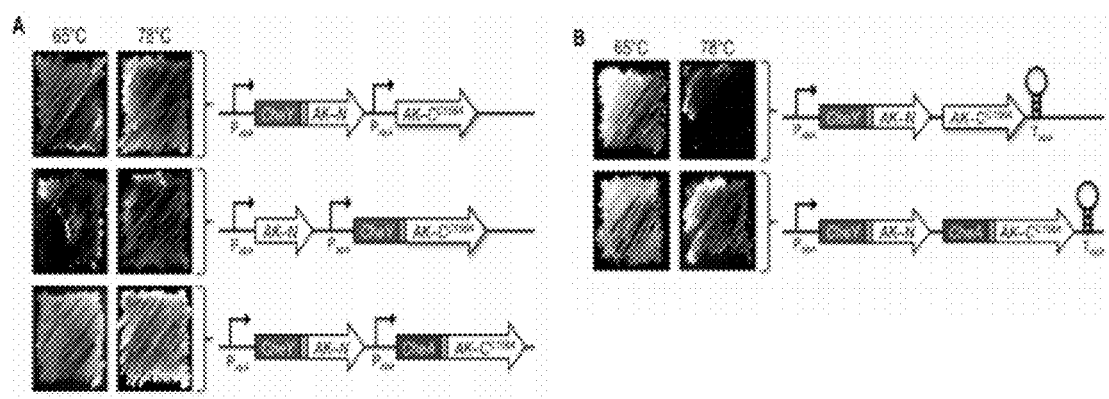
FIGS. 6A-6B illustrate the constructs of different combinations of adenylate kinase fragments and CheA/CheY genes and the results of complementation assay.

Additionally, complementation of PQN1 by coexpressing *T. Maritima* CheA and CheY proteins was also tested. FIG. 6A shows the results from complementation studies examining interaction between *T. maritima* CheA and CheY, proteins that have been shown to bind at temperatures as high as 70° C. While coexpression of AK fragments fused to CheA and CheY supported the growth of PQN1, as predicted, this complementation cannot be interpreted as arising from CheA-CheY interaction since growth was observed when only one of the AK fragments was fused to CheY. We hypothesized that CheY alone promotes PQN1 growth because its extreme thermostability (T$_m$>100° C.) stabilizes the AK fragments and the strong slpA promoter (P$_{slpA}$) without transcriptional terminators leads to high transcription and fragment accumulation.

To test this, vectors were created that produce both AK fragments from a single transcript with multiple ribosomal binding sites. FIG. 6B shows that with this expression strategy AK fragments fused to a single CheY were not able to support PQN1 growth at 78° C. In contrast, AK fragments fused to CheA and CheY complement PQN1, indicating that AK fragment complementation can be used to detect CheA and CheY binding at 78° C. by simply tuning down protein expression.

Example 4

AK Variants

In addition to the adenylate kinase split at position 79 tested above, we have made a great many additional mutants and tested their ability to self complement at mesophilic temperatures. Unlike the adenylate kinase protein from mesophilic bacteria, the adenylate kinase from the thermophilic bacteria is much more tolerant of fragmentation, and will still self assemble to produce function adenylate kinase activity. In fact, we identified a higher fraction of functional variants in the *T. neapolitana* library (41%) than with the *B. subtilis* library (27%). This data is extremely voluminous, and is therefore not shown, but only summarized herein.

Many functional variants were found that were split throughout the AMP binding site, the core, and the lid domains of *T. neapolitana* adenylate kinase, but DNA sequencing of unselected variants from the libraries identified fragmentation sites dispersed throughout the entire adk coding sequence.

We also discovered that the *T. neapolitana* adenylate kinase is more tolerant of truncation. Indeed, strongly functional variants were discovered that lack up to 31 residues, which correspond to α-helix 9, β-sheet 8, and a portion of α-helix 8 observed in the *B. subtilis* AK crystal structure. In contrast, *B. subtilis* adenylate kinase truncations lacking 22 and 31 residues are not able to support *E. coli* CV2 growth at 40° C.

Therefore, we believe that a great many variations in both thermophilic AK sequence will function in the claimed assay, and also that the fragmentation can occur at most points throughout the adenylate kinase, and that many truncations all also functional.

To summarize—We have provided evidence that AK fragment complementation in *T. thermophilus* is proportional to the thermostability of the protein being fragmented, as previously observed in *E. coli*. Whereas $AK_{Tn}$ fragments alone could complement PQN1 at 78° C., fragments with mutations in the cysteines that coordinate a thermostabilizing $Zn^{+2}$ (Glaser, et al. 1992, Vieille, et al. 2003) could not support PQN1 growth at this temperature. However, $AK_{Tn}$ fragments harboring the destabilizing C156A mutation were able to complement PQN1 when they were fused to chemotaxis proteins that homodimerize (CheX) and heterodimerize ($CheA^{P1P2}$ and CheY). Therefore, the complementation assay was successful in a living thermophile at physiological temperatures.

This indicates that covalent linkage to associating proteins can drive the reassembly of the $AK_{Tn}$ fragments harboring the C156A mutation at 78° C., greatly extending the temperature range where a split AK can be used as a protein complementation assay from mesophile to thermophile to hyperthermophile temperatures.

The finding that the TnN and TnC fragments cooperatively function at 78° C. upon heterologous expression also reinforces the hypothesis that the ability of a protein to fold and function at extreme temperatures is intrinsically encoded by its amino acid sequence, and this suggests that these $AK_{Tn}$ polypeptides may be useful for creating a protein complementation assay that functions at even higher temperatures than those tested herein, although at the highest temperatures it is expected that the CYS mutations to decrease zinc binding may not be needed.

Our studies examining the effects of *T. maritima* chemotaxis proteins on $AK_{Tn}$-fragment complementation increases the maximum temperature (78° C.) where an interaction has been observed between the kinase $CheA^{P1P2}$ and its target CheY. PQN1 growth was complemented by a vector that expresses $AK_{Tn}$ fragments fused to $CheA^{P1P2}$ and CheY but not by vectors that express $AK_{Tn}$ fragments fused to only one of these chemotaxis proteins.

This is consistent with our findings from light scattering measurements performed at 78° C., which revealed that a mixture of purified $CheA^{P1P2}$ and CheY exhibits an average hydrodynamic diameter that is greater than either of the individual proteins. Measurements of CheX-assisted fragment complementation also provides evidence that the CheX phosphatase self-associates at the temperature where it functions in *T. maritima*. PQN1 growth was complemented at 78° C. by a vector that coexpresses CheX-TnN and CheX-$TnC^{C156A}$ to a much greater extent than vectors that express only one of the two $AK_{Tn}$ fragments as a fusion with CheX.

The high-temperature protein fragment complementation assay described herein is expected to have several advantages in discovering interactions among natural and engineered proteins compared with previously described approaches, such as mesophilic two-hybrid and PCA screens. The $AK_{Tn}$-based complementation assay is implemented within a *T. thermophilus* HB8 strain growing at a temperature where many thermophiles and hyperthermophiles grow, making it better suited for discovering interactions among proteins that have evolved to fold and function at extreme temperatures. In addition, this selection is expected to be more sensitive than existing assays at detecting interactions among proteins whose free energy of binding increases as temperature decreases below the physiological growth range of thermotolerant microbes.

Our $AK_{Tn}$-based protein complementation assay should also aid protein design efforts working to create artificial protein complexes that are stable at the temperatures where thermophiles and hyperthermophiles grow. This novel protein complementation assay can be used as a high-throughput screen to evaluate the association of proteins created through rational design and laboratory evolution.

In addition, this protein complementation assay can be used to investigate the robustness of protein complexes to different mutational processes and to examine why some hyperthermophilic protein complexes weaken in affinity as temperature is decreased below the physiological growth range of hyperthermophiles, whereas other do not. The latter problem can be addressed by mining libraries of engineered (or natural) proteins for interactions that occur at 78° C. and re-screening discovered variants for decreased association at 40° C., using a structurally-related protein complementation assay that was developed for use in *E. coli* at 40° C. By comparing the sequences of the protein complexes that support protein complementation to different extents at high and low temperatures, hypotheses about the biophysical origin of these observations can be tested.

The following references are incorporated by reference herein in their entirety:

Bae, E., and Phillips, G. N., Jr., Structures and analysis of highly homologous psychrophilic, mesophilic, and thermophilic adenylate kinases, J. Biol. Chem. 279: 28202-28208 (2004).

Brouns, S. J., et al., Engineering a selectable marker for hyperthermophiles, J. Biol. Chem. 280: 11422-11431 (2005).

Cameron, D. M., et al., *Thermus thermophilus* L11 methyltransferase, PrmA, is dispensable for growth and preferentially modifies free ribosomal protein L11 prior to ribosome assembly, J. Bacteriol. 186: 5819-5825 (2004)

Faraldo, M. M., et al., Sequence of the S-layer gene of *Thermus thermophilus HB8* and functionality of its promoter in *Escherichia coli*, J. Bacteriol. 174:7458-7462 (1992).

Glaser, P., et al., Zinc, a novel structural element found in the family of bacterial adenylate kinases, Biochemistry 31: 3038-3043 (1992)

Hoseki, J., et al., Directed evolution of thermostable kanamycin-resistance gene: a convenient selection marker for *Thermus thermophilus*, J. Biochem. (Tokyo) 126, 951-956. (1999)

Nguyen, P. Q., et al., Thermostability promotes the cooperative function of split adenylate kinases, Protein Eng. Des. Sel. 21:303-310 (2008)

Park, S. Y., et al., In different organisms, the mode of interaction between two signaling proteins is not necessarily conserved, Proc. Natl. Acad. Sci. USA 101: 11646-11651 (2004).

Park, S. Y., et al., Structure and function of an unusual family of protein phosphatases: the bacterial chemotaxis proteins CheC and CheX, Mol. Cell. 16: 563-574.

Vieille, C., et al., *Thermotoga neapolitana* adenylate kinase is highly active at 30 degrees C., Biochem. J. 372:577-585 (2003)

What is claimed is:

1. A protein fragment complementation assay for thermophilic bacteria, comprising:
   a) culturing a thermophilic bacteria at a temperature greater than 70° C.,
      i) wherein said thermophilic bacteria comprises a native adenylate kinase that is replaced with a temperature-sensitive adenylate kinase that does not function at temperatures of above 70° C.,
      ii) a first vector having an expressable first test gene fused in frame to a first portion of a nucleic acid encoding a first portion of a thermostable adenylate kinase having at least 50% activity at temperature greater than 70° C.,
      iii) a second vector having an expressable second test gene fused in frame to a nucleic acid encoding a second portion of a thermostable adenylate kinase having at least 50% activity at temperature greater than 70° C.,
      iv) wherein association of a first test peptide and a second test peptide allows association of the first and second portions of the thermostable adenylate kinases and growth of the thermophilic bacteria at a temperature greater than 70° C.,
   b) and assaying for growth of said thermophilic bacteria, wherein growth indicates that said first test and said second test peptides associate in vivo.

2. The protein complementation assay of claim 1, wherein the first and second portions are split at residue 79 or 80, said residue numbered in accordance with SEQ ID NO. 1, and said first and second portions originate from the same adenylate kinase or from different adenylate kinases.

3. The protein complementation assay of claim 1, wherein the thermostable adenylate kinase has about 50% identity to SEQ ID NO. 1.

4. The protein complementation assay of claim 1, wherein the thermostable adenylate kinase has at least 60% identity to SEQ ID NO. 1.

5. The protein complementation assay of claim 1, wherein the thermostable adenylate kinase has at least 92% identity to SEQ ID NO. 1.

6. The protein complementation assay of claim 1, wherein the thermostable adenylate kinase has a sequence selected from the group consisting of SEQ ID NOs. 1, 2, 3, 4, and 5.

7. The protein complementation assay of claim 1, wherein the first and second portions are selected from residues 1-79 and 80-220 of the thermostable adenylate kinase of SEQ ID NOs. 1, 2, 3, 4, and 5, said residues numbered in accordance with SEQ ID NO. 1.

8. The protein complementary assay of claim 1, wherein the first and second test genes are polycistronic.

9. The protein complementation assay of claim 1, wherein the thermostable adenylate kinase comprises a mutated cysteine residue and binds less zinc than a wild type thermostable adenylate kinase.

10. The protein complementation assay of claim 1, wherein the second portion comprises Cys133Ala or Cys156Ala, said Cys numbered in accordance with SEQ ID NO. 1.

11. The protein complementation assay of claim 8, wherein the second portion comprises Cys133Ala or Cys156Ala, said Cys numbered in accordance with SEQ ID NO. 1.

12. The protein complementary assay of claim 1, wherein said test genes are each separated from said adenylate kinase portions with a flexible linker sequence.

13. The protein complementary assay of claim 1, wherein the bacteria is hyperthermophilic, the temperature sensitive adenylate kinase does not function at temperatures of at least 78° C., and the association of the first and second portion of the thermostable adenylate kinase allows growth of the hyperthermophilic bacteria at temperatures of at least 78° C.

14. The protein complementary assay of claim 1, wherein the first and second vectors are the same vector and the first and second portions of the thermostable adenylate kinase are polycistronic.

15. The protein complementary assay of claim 1, wherein the first and second portions of the thermostable adenylate kinase are selected from the group consisting of:
    a) residues 1-79 or 80-220 from SEQ ID NO. 1;
    b) residues 1-79 or 80-220 from SEQ ID NO. 2;
    c) residues 1-79 or 80-220 from SEQ ID NO. 3;
    d) residues 1-79 or 80-220 from SEQ ID NO. 4;
    e) residues 2-80 or 81-220 from SEQ ID NO. 5; and mixed species combinations thereof.

* * * * *

SEQUENCE LISTING

<160> NUMBER OF SEQ ID NOS: 32

<210> SEQ ID NO 1
<211> LENGTH: 220
<212> TYPE: PRT
<213> ORGANISM: Thermotoga neapolitana

<400> SEQUENCE: 1

```
Met Met Ala Tyr Leu Val Phe Leu Gly Pro Pro Gly Ala Gly Lys Gly
1               5                   10                  15

Thr Tyr Ala Lys Arg Ile Gln Glu Lys Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Lys Gly Glu Leu Val Pro Asp
    50                  55                  60

Glu Leu Val Asn Glu Val Val Lys Arg Arg Leu Ser Glu Lys Asp Cys
65                  70                  75                  80

Glu Lys Gly Phe Ile Leu Asp Gly Tyr Pro Arg Thr Val Ala Gln Ala
                85                  90                  95

Glu Phe Leu Asp Ser Phe Leu Glu Ser Gln Asn Lys Gln Leu Thr Ala
            100                 105                 110

Ala Val Leu Phe Asp Val Pro Glu Asp Val Val Gln Arg Leu Thr
        115                 120                 125

Ser Arg Arg Ile Cys Pro Lys Cys Gly Arg Ile Tyr Asn Met Ile Ser
    130                 135                 140

Leu Pro Pro Lys Glu Asp Glu Leu Cys Asp Asp Cys Lys Val Lys Leu
145                 150                 155                 160

Val Gln Arg Asp Asp Asp Lys Glu Glu Thr Val Arg His Arg Tyr Lys
                165                 170                 175

Val Tyr Leu Glu Lys Thr Gln Pro Val Ile Asp Tyr Tyr Gly Lys Lys
            180                 185                 190

Gly Ile Leu Lys Arg Val Asp Gly Thr Ile Gly Ile Asp Asn Val Val
        195                 200                 205

Ala Glu Val Leu Lys Ile Ile Gly Trp Ser Asp Lys
    210                 215                 220
```

<210> SEQ ID NO 2
<211> LENGTH: 220
<212> TYPE: PRT
<213> ORGANISM: Thermotoga maritima

<400> SEQUENCE: 2

```
Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
    50                  55                  60

Glu Leu Val Asn Glu Val Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95
```

```
Glu Phe Leu Asp Asp Phe Leu Lys Asn Gln Asn Lys Glu Leu Thr Ala
            100                 105                 110

Ala Val Leu Phe Glu Val Pro Glu Val Val Gln Arg Leu Thr
            115                 120                 125

Ala Arg Arg Ile Cys Pro Lys Cys Gly Arg Ile Tyr Asn Leu Ile Ser
130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
            165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
            195                 200                 205

Ala Glu Val Leu Lys Ile Val Gly Trp Ser Asp Lys
210                 215                 220

<210> SEQ ID NO 3
<211> LENGTH: 220
<212> TYPE: PRT
<213> ORGANISM: Thermotoga naphthophila

<400> SEQUENCE: 3

Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
            35                  40                  45

Gly Lys Lys Ile Lys Glu Ile Met Glu Arg Gly Glu Leu Val Pro Asp
        50                  55                  60

Glu Leu Val Asn Glu Val Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
            85                  90                  95

Glu Phe Leu Asp Asp Phe Leu Lys Thr Gln Asn Lys Glu Leu Thr Ala
            100                 105                 110

Ala Ile Leu Phe Glu Val Pro Glu Glu Val Val Gln Arg Leu Thr
            115                 120                 125

Ala Arg Arg Ile Cys Pro Lys Cys Gly Arg Ile Tyr Asn Leu Ile Ser
130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
            165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
            195                 200                 205

Ala Glu Val Leu Lys Ile Ile Gly Trp Ser Asp Lys
210                 215                 220

<210> SEQ ID NO 4
<211> LENGTH: 220
<212> TYPE: PRT
<213> ORGANISM: Thermotoga petrophila
```

-continued

<400> SEQUENCE: 4

Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
    50                  55                  60

Glu Leu Val Asn Glu Val Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95

Glu Phe Leu Asp Asp Phe Leu Lys Asn Gln Asn Lys Glu Leu Thr Ala
            100                 105                 110

Ala Val Leu Phe Glu Val Pro Glu Glu Val Val Gln Arg Leu Thr
        115                 120                 125

Ala Arg Arg Ile Cys Pro Lys Cys Gly Arg Ile Tyr Asn Leu Ile Ser
    130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
                165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
        195                 200                 205

Ala Glu Val Leu Lys Ile Val Gly Trp Ser Asp Lys
    210                 215                 220

<210> SEQ ID NO 5
<211> LENGTH: 219
<212> TYPE: PRT
<213> ORGANISM: Marinitoga piezophila

<400> SEQUENCE: 5

Met Ala Tyr Leu Val Phe Leu Gly Pro Pro Gly Ala Gly Lys Gly Thr
1               5                   10                  15

Tyr Ala Lys Arg Leu Gln Glu Ile Thr Gly Ile Pro His Ile Ser Thr
            20                  25                  30

Gly Asp Ile Phe Arg Asp Ile Val Lys Lys Glu Asn Asp Glu Leu Gly
        35                  40                  45

Lys Lys Ile Lys Glu Ile Met Glu Arg Gly Glu Leu Val Pro Asp Glu
    50                  55                  60

Leu Val Asn Glu Val Val Lys Arg Arg Leu Ser Glu Lys Asp Cys Glu
65                  70                  75                  80

Arg Gly Phe Ile Leu Asp Gly Tyr Pro Arg Thr Val Ala Gln Ala Glu
                85                  90                  95

Phe Leu Asp Asp Phe Leu Lys Asn Gln Asn Lys Glu Leu Thr Ala Ala
            100                 105                 110

Val Leu Phe Glu Val Pro Glu Glu Val Val Gln Arg Leu Thr Ala
        115                 120                 125

Arg Arg Ile Cys Pro Lys Cys Gly Arg Ile Tyr Asn Leu Ile Ser Leu
    130                 135                 140

Pro Pro Lys Glu Asp Glu Leu Cys Asp Asp Cys Lys Val Lys Leu Val

```
            145                 150                 155                 160
Gln Arg Glu Asp Asp Lys Glu Thr Val Arg His Arg Tyr Lys Val
                165                 170                 175

Tyr Leu Glu Lys Thr Gln Pro Val Ile Asp Tyr Asp Lys Lys Gly
            180                 185                 190

Ile Leu Lys Arg Val Asp Gly Thr Ile Gly Ile Asp Asn Val Ile Ala
        195                 200                 205

Glu Val Leu Lys Ile Val Gly Trp Ser Asp Lys
    210                 215

<210> SEQ ID NO 6
<211> LENGTH: 214
<212> TYPE: PRT
<213> ORGANISM: Thermosipho melanesiensis BI429

<400> SEQUENCE: 6

Met Asn Ile Val Phe Leu Gly Pro Pro Gly Ala Gly Lys Gly Thr Tyr
1               5                   10                  15

Ala Lys Glu Leu Lys Glu Ile Leu Gly Ile Pro His Ile Ser Thr Gly
            20                  25                  30

Asp Met Phe Arg Glu Glu Ile Ser Ala Lys Ser Glu Leu Gly Arg Lys
        35                  40                  45

Val Glu Asp Ile Leu Lys Arg Gly Glu Leu Val Pro Asp Asp Leu Thr
    50                  55                  60

Asn Val Ile Val Lys Glu Arg Leu Ser Lys Pro Asp Cys Lys Lys Gly
65                  70                  75                  80

Phe Ile Leu Asp Gly Tyr Pro Arg Thr Val Ala Gln Ala Lys Ala Leu
                85                  90                  95

Asp Glu Ile Leu Lys Lys Leu Gly Arg Glu Leu Lys Phe Ala Ile Tyr
            100                 105                 110

Phe Glu Val Ser Glu Asp Val Val Lys Arg Ile Ser Asn Arg Arg
        115                 120                 125

Ile Cys Lys Asn Cys Gly Lys Ile Tyr Asn Leu Ile Thr Leu Pro Pro
    130                 135                 140

Lys Ile Asn Gly Lys Cys Asp Val Cys Gly Gly Glu Leu Tyr Gln Arg
145                 150                 155                 160

Glu Asp Asp Arg Glu Glu Val Val Arg Arg Tyr Lys Val Tyr Met
                165                 170                 175

Asp Asn Thr Tyr Pro Val Ile Glu Tyr Tyr Arg Lys Ser Asn Lys Leu
            180                 185                 190

Phe Thr Val Asp Gly Ser Met Asp Val Asp Ser Val Ile Lys Glu Val
        195                 200                 205

Leu Asn Ile Ile Arg Arg
    210

<210> SEQ ID NO 7
<211> LENGTH: 214
<212> TYPE: PRT
<213> ORGANISM: Thermosipho africanus TCF52B

<400> SEQUENCE: 7

Met Asn Met Val Phe Leu Gly Pro Pro Gly Ala Gly Lys Gly Thr Tyr
1               5                   10                  15

Ala Lys Arg Leu Ile Glu Met Leu Asn Ile Pro His Ile Ser Thr Gly
            20                  25                  30

Asp Met Phe Arg Glu Ala Val Ala Ser Lys Ser Glu Leu Gly Lys Lys
        35                  40                  45
```

Val Glu Glu Ile Leu Lys Arg Gly Asp Leu Val Pro Asp Asp Leu Thr
        50                  55                  60

Asn Ser Ile Val Lys Asp Arg Leu Ser Lys Glu Asp Cys Lys Asn Gly
 65                  70                  75                  80

Phe Ile Leu Asp Gly Phe Pro Arg Thr Val Ala Gln Ala Lys Ala Leu
                 85                  90                  95

Asp Glu Ile Met Arg Ser Leu Gly Lys Asp Leu Asp Tyr Val Ile Tyr
                100                 105                 110

Phe Glu Val Asp Glu Glu Val Val Lys Arg Ile Ser Asn Arg Arg
            115                 120                 125

Ile Cys Ser Asn Cys Gly Lys Ile Tyr Asn Leu Ile Thr Leu Pro Pro
130                 135                 140

Lys Val Asp Gly Lys Cys Asp Val Cys Gly Gly Thr Leu Tyr Gln Arg
145                 150                 155                 160

Glu Asp Asp Lys Glu Glu Val Val Arg Lys Arg Tyr Arg Val Tyr Met
                165                 170                 175

Glu Asn Thr Tyr Pro Val Ile Glu Tyr Tyr Gln Lys Ser Asn Lys Leu
                180                 185                 190

Phe Thr Val Asn Gly Ala Leu Asp Val Asp Ser Val Ile Lys Glu Val
            195                 200                 205

Leu Asn Ile Ile Arg Arg
        210

<210> SEQ ID NO 8
<211> LENGTH: 218
<212> TYPE: PRT
<213> ORGANISM: Fervidobacterium nodosum Rt17-B1

<400> SEQUENCE: 8

Met Asn Leu Ile Phe Leu Gly Pro Pro Gly Ala Gly Lys Gly Thr Tyr
  1               5                  10                  15

Ala Lys Arg Val Val Glu Lys Tyr Ile Ile Pro His Ile Ser Thr Gly
                 20                  25                  30

Asp Ile Phe Arg Glu Ala Ile Ala Lys Gly Thr Glu Leu Gly Arg Lys
             35                  40                  45

Val Gln Asp Ile Val Asn Ser Gly Asn Leu Val Pro Asp Glu Leu Thr
        50                  55                  60

Asn Ala Leu Val Glu Glu Arg Leu Lys Gln Asp Asp Cys Lys Lys Gly
 65                  70                  75                  80

Phe Ile Leu Asp Gly Tyr Pro Arg Thr Leu Asn Gln Ala Gln Ala Leu
                 85                  90                  95

Asn Glu Met Leu Lys Lys Met Gly Lys Glu Leu Asp Gly Ala Ile Tyr
                100                 105                 110

Phe Glu Val Asp Glu Glu Thr Val Val Gln Arg Ile Ser Thr Arg Arg
            115                 120                 125

Val Cys Ser Lys Cys Gly Lys Val Tyr Asn Val Ile Thr Leu Pro Ser
130                 135                 140

Lys Val Glu Gly Ile Cys Asp Asp Cys Gly Gly Thr Leu Ile Gln Arg
145                 150                 155                 160

Asp Asp Asp Lys Glu Asp Ile Val Arg Ser Arg Tyr Arg Val Tyr Ile
                165                 170                 175

Glu Lys Thr Ser Pro Leu Ile Glu Tyr Tyr Lys Asn Gln Asn Lys Leu
                180                 185                 190

Phe Thr Leu Asp Gly Arg Lys Ser Val Glu Glu Val Met Lys Ile Leu
            195                 200                 205

```
Phe Asn Ile Leu Gly Gly Phe Glu Lys Lys
    210                 215
```

```
<210> SEQ ID NO 9
<211> LENGTH: 217
<212> TYPE: PRT
<213> ORGANISM: Archaeoglobus fulgidus DSM 4304

<400> SEQUENCE: 9

Met Asn Leu Ile Phe Leu Gly Pro Pro Gly Ala Gly Lys Gly Thr Gln
1               5                   10                  15

Ala Lys Arg Val Ser Glu Lys Tyr Gly Ile Pro Gln Ile Ser Thr Gly
            20                  25                  30

Asp Met Leu Arg Glu Ala Val Ala Lys Gly Thr Glu Leu Gly Lys Lys
        35                  40                  45

Ala Lys Glu Tyr Met Asp Lys Gly Glu Leu Val Pro Asp Glu Val Val
    50                  55                  60

Ile Gly Ile Val Lys Glu Arg Leu Gln Gln Pro Asp Cys Glu Lys Gly
65                  70                  75                  80

Phe Ile Leu Asp Gly Phe Pro Arg Thr Leu Ala Gln Ala Glu Ala Leu
                85                  90                  95

Asp Glu Met Leu Lys Glu Leu Asn Lys Lys Ile Asp Ala Val Ile Asn
            100                 105                 110

Val Val Val Pro Glu Glu Glu Val Lys Arg Ile Thr Tyr Arg Arg
            115                 120                 125

Thr Cys Arg Asn Cys Gly Ala Val Tyr His Leu Ile Tyr Ala Pro Pro
        130                 135                 140

Lys Glu Asp Asn Lys Cys Asp Lys Cys Gly Gly Glu Leu Tyr Gln Arg
145                 150                 155                 160

Asp Asp Asp Lys Glu Glu Thr Val Arg Glu Arg Tyr Arg Val Tyr Lys
                165                 170                 175

Gln Asn Thr Glu Pro Leu Ile Asp Tyr Tyr Arg Lys Lys Gly Ile Leu
            180                 185                 190

Tyr Asp Val Asp Gly Thr Lys Asp Ile Glu Gly Val Trp Lys Glu Ile
        195                 200                 205

Glu Ala Ile Leu Glu Lys Ile Lys Ser
    210                 215
```

```
<210> SEQ ID NO 10
<211> LENGTH: 218
<212> TYPE: PRT
<213> ORGANISM: Ferroglobus placidus DSM 10642

<400> SEQUENCE: 10

Met Asn Leu Ile Leu Leu Gly Pro Pro Gly Ala Gly Lys Gly Thr Gln
1               5                   10                  15

Ala Lys Met Ile Val Glu Lys Tyr Gly Ile Pro Gln Ile Ser Thr Gly
            20                  25                  30

Asp Ile Leu Arg Glu Ala Val Ala Lys Gly Thr Glu Leu Gly Arg Lys
        35                  40                  45

Ala Lys Glu Tyr Met Asp Arg Gly Glu Leu Val Pro Asp Glu Val Val
    50                  55                  60

Ile Gly Ile Val Arg Glu Arg Leu Ser Gln Pro Asp Cys Glu Lys Gly
65                  70                  75                  80

Phe Ile Leu Asp Gly Phe Pro Arg Thr Val Arg Gln Ala Glu Ala Leu
                85                  90                  95
```

```
Asp Glu Met Leu Asp Glu Met Gly Arg Lys Ile Asp Ala Val Ile Ser
            100                 105                 110

Ile Glu Val Pro Glu Glu Ile Val Lys Arg Ile Val Tyr Arg Arg
        115                 120                 125

Ile Cys Lys Gln Cys Gly Ala Val Tyr Asn Leu Ile Tyr Asn Pro Pro
        130                 135                 140

Lys Val Asp Gly Lys Cys Asp Lys Cys Gly Gly Glu Leu Tyr Gln Arg
145                 150                 155                 160

Asp Asp Asp Lys Glu Glu Val Val Arg Glu Arg Tyr Arg Val Tyr Lys
                165                 170                 175

Glu Gln Thr Glu Pro Leu Lys Gly Tyr Tyr Arg Arg Thr Gly Val Leu
            180                 185                 190

Tyr Glu Val Asp Gly Thr Lys Ser Ile Glu Glu Val Phe Asn Glu Ile
        195                 200                 205

Asp Ser Ile Leu Gln Lys Ile Ser Lys Gly
        210                 215
```

<210> SEQ ID NO 11
<211> LENGTH: 215
<212> TYPE: PRT
<213> ORGANISM: Petrotoga mobilis SJ95

<400> SEQUENCE: 11

```
Met Arg Leu Leu Phe Phe Gly Pro Pro Gly Ala Gly Lys Gly Thr Gln
1               5                   10                  15

Ala Lys Lys Val Ala Gln Glu Phe Gln Ile Val His Ile Ser Thr Gly
            20                  25                  30

Asp Ile Leu Arg Asp Ala Val Ser Lys Gly Thr Glu Leu Gly Lys Met
        35                  40                  45

Ala Lys Ala Ile Met Asp Arg Gly Glu Leu Val Ser Asp Glu Ile Met
50                  55                  60

Asn Ser Leu Val Lys Glu Arg Leu Glu Glu Leu Asp Ser Phe Ile Leu
65                  70                  75                  80

Asp Gly Tyr Pro Arg Thr Leu Asp Gln Ala Lys Phe Leu Asp Gln Ala
                85                  90                  95

Thr Lys Glu Leu Gln Lys Glu Ile Asp Ala Ala Val Leu Ile Asp Val
            100                 105                 110

Ser Glu Glu Glu Ile Val Lys Arg Ile Ser Asn Arg Val Cys Pro
        115                 120                 125

Asn Cys Gly Lys Val Tyr Asn Leu Ile Thr Leu Gln Pro Lys Glu Asp
130                 135                 140

Glu Lys Cys Asp Val Cys Gly Thr Lys Leu Ile Gln Arg Asp Asp Asp
145                 150                 155                 160

Lys Glu Glu Val Val Arg Glu Arg Tyr Lys Val Tyr Lys Lys Asn Thr
                165                 170                 175

Glu Pro Val Ile Glu Tyr Tyr Arg Lys Asn Asn Lys Ile Ile Thr Ile
            180                 185                 190

Asp Gly Ala Gln Asn Val Glu Asp Val Thr Lys Glu Leu Phe Asn Ile
        195                 200                 205

Leu Arg Ser Phe Asn Lys Gln
        210                 215
```

<210> SEQ ID NO 12
<211> LENGTH: 217
<212> TYPE: PRT
<213> ORGANISM: Thermotoga lettingae TMO -continued

```
<400> SEQUENCE: 12

Met Lys Ile Val Leu Leu Gly Ala Pro Gly Ala Gly Lys Gly Thr Leu
1               5                   10                  15

Ala Lys Asp Leu Ser Ile Met Phe Ser Val Pro His Ile Ser Thr Gly
            20                  25                  30

Asp Met Phe Arg Glu Ala Val Ala Ala Gly Thr Glu Leu Gly Val Lys
        35                  40                  45

Val Gln Asn Ile Leu Ser Ser Gly Ala Leu Val Pro Asp Glu Ile Val
50                  55                  60

Asn Gln Val Val Glu Glu Arg Leu Arg Lys Gln Asp Cys Glu Lys Gly
65                  70                  75                  80

Phe Ile Phe Asp Gly Tyr Pro Arg Thr Ile Ala Gln Ala Ile Ala Leu
                85                  90                  95

Asp Glu Ile Leu Gln Lys Met Ser Lys Lys Leu Asp Leu Ala Ile Tyr
            100                 105                 110

Leu Glu Ala Ser Glu Glu Thr Val Val Lys Arg Leu Thr Ser Arg Arg
        115                 120                 125

Ile Cys Pro Lys Cys Gly Lys Ile Tyr Asn Leu Ile Ser Met Pro Pro
130                 135                 140

Val Ser Asp Gln Ile Cys Asp Cys Gly Glu Gln Leu Val Ile Arg
145                 150                 155                 160

Glu Asp Asp Lys Glu Glu Val Val Arg Lys Arg Tyr Arg Leu Tyr Leu
                165                 170                 175

Glu Thr Thr Ala Pro Leu Val Gly Tyr Tyr Ser Gly Arg Asp Ile Leu
            180                 185                 190

Val Ser Val Asn Ser Glu Arg Asp His Arg Lys Leu Val Glu Asp Val
        195                 200                 205

Ser Arg Leu Leu Lys Lys Val Ile Ser
            210                 215

<210> SEQ ID NO 13
<211> LENGTH: 215
<212> TYPE: PRT
<213> ORGANISM: Dictyoglomus thermophilum H-6-12

<400> SEQUENCE: 13

Met Met Lys Ala Ile Ile Phe Leu Gly Pro Pro Gly Ala Gly Lys Gly
1               5                   10                  15

Thr His Ala Lys Glu Val Ser Gln Ile Leu Asn Ile Pro His Ile Ser
            20                  25                  30

Thr Gly Asp Ile Phe Arg Glu His Val Lys Asn Gln Thr Glu Leu Gly
        35                  40                  45

Ile Lys Val Lys Ser Tyr Leu Asp Ser Gly Ser Leu Val Pro Asp Glu
50                  55                  60

Leu Val Trp Glu Val Val Lys Asp Arg Ile Ser Lys Glu Asp Cys Lys
65                  70                  75                  80

Asn Gly Phe Ile Leu Asp Gly Phe Pro Arg Thr Ile Pro Gln Ala Glu
                85                  90                  95

Met Leu Glu Lys Tyr Leu Lys Glu Lys Asn Ala Val Ile Lys Val Ile
            100                 105                 110

Tyr Leu Asp Ala Ser Asp Glu Leu Val Ile Lys Arg Leu Ser Ala Arg
        115                 120                 125

Arg Val Cys Lys Asn Cys Gly Ala Ile Tyr Asn Leu Ile Ser Met Pro
130                 135                 140

Pro Lys Lys Asp Gly Ile Cys Asp Ile Cys Gly Gly Glu Leu Tyr Gln
```

```
              145                 150                 155                 160
Arg Ser Asp Asp Lys Pro Glu Val Ile Lys Gln Arg Leu Glu Thr Tyr
                    165                 170                 175

Tyr Lys Glu Thr Gln Pro Leu Ile Asp Tyr Tyr Arg Asn Lys Gly Ile
                180                 185                 190

Met Tyr Thr Ile Ser Ala Glu Lys Glu Arg Glu Glu Val Leu Asn Glu
            195                 200                 205

Ile Leu Lys Val Ile Ser Glu
        210                 215

<210> SEQ ID NO 14
<211> LENGTH: 213
<212> TYPE: PRT
<213> ORGANISM: Hydrogenivirga sp. 128-5-R1-1

<400> SEQUENCE: 14

Met Arg Lys Asn Leu Val Phe Leu Gly Pro Pro Gly Ala Gly Lys Gly
1               5                   10                  15

Thr Gln Ala Lys Arg Leu Ala Gln Glu Leu Gly Leu Met His Ile Ser
            20                  25                  30

Thr Gly Asp Ile Leu Arg Glu Ala Val Lys Lys Gly Thr Pro Leu Gly
        35                  40                  45

Lys Lys Ala Lys Glu Tyr Met Asp Lys Gly Glu Leu Val Pro Asp Asp
    50                  55                  60

Leu Ile Val Ala Leu Ile Glu Glu Val Met Pro Pro Glu Gly Gly Val
65                  70                  75                  80

Ile Phe Asp Gly Phe Pro Arg Thr Ile Ala Gln Ala Glu Ala Leu Asp
                85                  90                  95

Glu Met Leu Ser Lys Lys Gly Met Gly Ile Asp Ala Val Val Leu Phe
            100                 105                 110

Asp Val Pro Asp Glu Val Val Glu Arg Leu Ser Gly Arg Arg Val
        115                 120                 125

Cys Pro Ser Cys Gly Ala Val Tyr His Ile Lys Phe Asn Pro Pro Glu
    130                 135                 140

Asn Asp Glu Val Cys Asp Arg Cys Gly Thr Lys Leu Ile Gln Arg Asp
145                 150                 155                 160

Asp Asp Arg Glu Glu Val Val Arg Asn Arg Leu Glu Val Tyr Arg Arg
                165                 170                 175

Gln Thr Glu Pro Leu Ile Glu Tyr Tyr Glu Arg Lys Gly Ile Leu Ile
            180                 185                 190

Arg Leu Asp Ala Ser Lys Glu Ile Glu Glu Val Tyr Gln Glu Leu Lys
        195                 200                 205

Lys Val Val Gly Ala
        210

<210> SEQ ID NO 15
<211> LENGTH: 217
<212> TYPE: PRT
<213> ORGANISM: Archaeoglobus profundus DSM 5631

<400> SEQUENCE: 15

Met Asn Ile Ile Leu Leu Gly Pro Pro Gly Gly Gly Lys Gly Thr Gln
1               5                   10                  15

Ala Lys Lys Ile Val Glu Lys Tyr Gly Ile Pro His Ile Ala Thr Gly
            20                  25                  30

Asp Ile Leu Arg Glu Ala Val Ala Lys Gly Thr Glu Leu Gly Lys Lys
        35                  40                  45
```

Ala Lys Glu Tyr Met Asp Arg Gly Glu Leu Val Pro Asp Glu Ile Val
    50                  55                  60

Ile Gly Ile Val Arg Glu Arg Leu Lys Gln Pro Asp Cys Glu Lys Gly
65                  70                  75                  80

Phe Leu Leu Asp Gly Phe Pro Arg Thr Leu Lys Gln Ala Glu Ala Leu
                85                  90                  95

Asp Glu Met Leu Lys Glu Leu Gly Lys Ser Ile Asp Ala Val Ile Tyr
            100                 105                 110

Ile Asp Val Pro Glu Glu Glu Val Lys Arg Ile Thr Tyr Arg Arg
            115                 120                 125

Thr Cys Arg Asn Cys Gly Ala Val Tyr His Leu Ile Tyr Ala Pro Pro
    130                 135                 140

Lys Glu Asp Asn Lys Cys Asp Lys Cys Gly Gly Glu Leu Tyr Gln Arg
145                 150                 155                 160

Asp Asp Asp Lys Glu Asp Val Val Arg Gln Arg Phe Lys Val Tyr Met
                165                 170                 175

Glu Asn Thr Ala Pro Leu Ile Glu Tyr Tyr Glu Lys Lys Gly Ile Leu
            180                 185                 190

Tyr Arg Val Asp Gly Thr Lys Ser Ile Asp Glu Val Phe Ala Gln Ile
            195                 200                 205

Asp Glu Ile Leu Gln Lys Ile Ala Lys
    210                 215

<210> SEQ ID NO 16
<211> LENGTH: 215
<212> TYPE: PRT
<213> ORGANISM: Thermodesulfovibrio yellowstonii DSM 11347

<400> SEQUENCE: 16

Met Arg Leu Val Phe Leu Gly Ala Pro Gly Ala Gly Lys Gly Thr Gln
1               5                   10                  15

Ala Lys Arg Leu Val Glu Lys Tyr Gly Ile Pro Gln Ile Ser Thr Gly
                20                  25                  30

Asp Leu Leu Arg Ala Ala Val Ala Ala Gly Thr Pro Leu Gly Lys Glu
            35                  40                  45

Ala Lys Ala Tyr Met Asp Arg Gly Glu Leu Val Pro Asp Lys Val Val
    50                  55                  60

Leu Gly Met Val Lys Glu Arg Leu Ser Gln Asn Asp Cys Lys Lys Gly
65                  70                  75                  80

Phe Ile Leu Asp Gly Phe Pro Arg Asn Val Ala Gln Ala Glu Ala Leu
                85                  90                  95

Asp Lys Met Leu Ser Glu Met Asn Met Pro Leu Asp Leu Ala Leu Asn
            100                 105                 110

Leu Asp Val Pro Phe Asp Leu Met Lys Arg Leu Thr Gly Arg Arg
            115                 120                 125

Thr Cys Lys Ser Cys Gly Gln Met Tyr Asn Val Tyr Tyr Ser Pro Ser
    130                 135                 140

Lys Val Glu Gly Lys Cys Asp Lys Cys Gly Gly Glu Leu Phe Gln Arg
145                 150                 155                 160

Asp Asp Asp Lys Glu Glu Thr Ile Arg Lys Arg Leu Glu Val Tyr Arg
                165                 170                 175

Ala Gln Thr Glu Pro Leu Ile Asp Tyr Tyr Ser Lys Lys Gly Ile Leu
            180                 185                 190

Lys Ser Val Ser Gly Thr Gly Ser Ile Asp Glu Ile Phe Asn Ser Ile
            195                 200                 205

```
Cys Ala Ile Leu Glu Lys Lys
    210             215

<210> SEQ ID NO 17
<211> LENGTH: 215
<212> TYPE: PRT
<213> ORGANISM: Dictyoglomus turgidum DSM 6724

<400> SEQUENCE: 17

Met Met Lys Ala Ile Ile Phe Leu Gly Pro Pro Gly Ala Gly Lys Gly
1               5                   10                  15

Thr His Ala Lys Glu Val Ser Gln Ile Leu Asn Ile Pro His Ile Ser
            20                  25                  30

Thr Gly Asp Ile Phe Arg Glu His Val Lys Asn Gln Thr Asp Leu Gly
        35                  40                  45

Ile Lys Val Lys Ser Tyr Leu Asp Ala Gly Lys Leu Val Pro Asp Glu
    50                  55                  60

Val Val Trp Glu Val Val Lys Asp Arg Ile Asp Lys Glu Asp Cys Lys
65                  70                  75                  80

Asn Gly Phe Ile Leu Asp Gly Phe Pro Arg Thr Ile Leu Gln Ala Glu
                85                  90                  95

Met Leu Glu Lys Tyr Leu Lys Glu Lys Asn Ala Asp Ile Lys Val Ile
            100                 105                 110

Tyr Leu Asp Ala Pro Asp Glu Leu Val Ile Arg Arg Leu Ser Ala Arg
        115                 120                 125

Arg Val Cys Lys Asn Cys Gly Ala Ile Tyr Asn Leu Ile Ser Met Pro
    130                 135                 140

Pro Lys Lys Asp Gly Ile Cys Asp Ile Cys Gly Gly Glu Leu Tyr Gln
145                 150                 155                 160

Arg Ser Asp Asp Lys Pro Glu Val Ile Lys Gln Arg Leu Glu Thr Tyr
                165                 170                 175

Tyr Lys Glu Thr Gln Pro Leu Ile Asp Tyr Tyr Lys Asn Lys Asp Ile
            180                 185                 190

Met Tyr Thr Ile Asn Ala Glu Lys Glu Arg Glu Glu Val Leu Lys Glu
        195                 200                 205

Ile Leu Lys Val Ile Asn Glu
    210             215

<210> SEQ ID NO 18
<211> LENGTH: 221
<212> TYPE: PRT
<213> ORGANISM: Thermoanaerobacter tengcongensis MB4

<400> SEQUENCE: 18

Met Arg Val Val Leu Leu Gly Pro Pro Gly Ala Gly Lys Gly Thr Gln
1               5                   10                  15

Ala Leu Lys Ile Ala Lys Glu Phe Asp Ile Pro His Ile Ser Thr Gly
            20                  25                  30

Asp Ile Phe Arg Gln Asn Leu Arg Asp Asn Thr Glu Leu Gly Lys Leu
        35                  40                  45

Ala Lys Glu Tyr Met Asp Lys Gly Leu Leu Val Pro Asp Glu Val Thr
    50                  55                  60

Asn Arg Ile Val Glu Asp Arg Leu Lys Glu Asp Cys Lys Lys Gly
65                  70                  75                  80

Phe Leu Leu Asp Gly Tyr Pro Arg Asn Ile Pro Gln Ala Glu Glu Leu
                85                  90                  95
```

Asp Lys Phe Leu Glu Glu Arg Gly His Ser Leu Thr Ala Val Ile Asn
                100                 105                 110

Ile Gln Val Glu Arg Glu Ala Leu Ile Asp Arg Ile Thr Gly Arg Arg
            115                 120                 125

Val Cys Pro Val Cys Gly Ala Thr Tyr His Ile Lys Thr Ser Pro Pro
        130                 135                 140

Lys Val Asp Asn Val Cys Asp Lys Cys Gly Ser Glu Leu Ile Gln Arg
145                 150                 155                 160

Ser Asp Asp Lys Leu Glu Ser Val Val Lys Arg Leu Glu Val Tyr Glu
                165                 170                 175

Lys Glu Thr Lys Pro Leu Ile Asp Tyr Tyr Thr Lys Lys Gly Ile Leu
            180                 185                 190

Val Asn Ile Asp Gly Asn Lys Ser Ile Asp Glu Val Phe Glu Asp Ile
        195                 200                 205

Lys Lys Ala Leu Leu Gly Asp Arg Arg Asp Asp Ile His
210                 215                 220

<210> SEQ ID NO 19
<211> LENGTH: 217
<212> TYPE: PRT
<213> ORGANISM: Thermoanaerobacter mathranii subsp. mathranii str. A3

<400> SEQUENCE: 19

Met Lys Ile Ile Leu Leu Gly Pro Pro Gly Ala Gly Lys Gly Thr Gln
1               5                   10                  15

Ala Lys Lys Ile Ala Lys Glu Phe Asp Ile Pro His Ile Ser Thr Gly
            20                  25                  30

Asp Ile Phe Arg Gln Asn Leu Arg Glu Asn Thr Asp Leu Gly Lys Leu
        35                  40                  45

Ala Lys Glu Tyr Met Asp Lys Gly Leu Leu Val Pro Asp Glu Val Thr
    50                  55                  60

Asn Lys Ile Val Glu Asn Arg Leu Glu Lys Asp Cys Gln Lys Gly
65                  70                  75                  80

Phe Leu Leu Asp Gly Tyr Pro Arg Asn Val Glu Gln Ala Glu Leu
                85                  90                  95

Asp Arg Phe Leu Gln Gly Lys Gly Ile His Leu Asp Cys Val Leu Asn
            100                 105                 110

Ile Glu Val Glu Lys Glu Ala Leu Ile Glu Arg Ile Thr Gly Arg Arg
        115                 120                 125

Val Cys Pro Asn Cys Gly Ala Thr Tyr His Ile Lys Thr Phe Pro Pro
    130                 135                 140

Thr Val Asp Asn Val Cys Asp Lys Cys Gly Ala Gln Leu Ile Gln Arg
145                 150                 155                 160

Ser Asp Asp Lys Leu Glu Ser Val Val Lys Arg Leu Glu Val Tyr Glu
                165                 170                 175

Ser Gln Thr Lys Pro Leu Ile Glu His Tyr Thr Lys Lys Gly Ile Leu
            180                 185                 190

Val Asn Ile Asp Gly Asn Lys Ser Val Glu Glu Val Phe Glu Asp Ile
        195                 200                 205

Lys Lys Val Leu Gly Asp Arg Gly Lys
210                 215

<210> SEQ ID NO 20
<211> LENGTH: 226
<212> TYPE: PRT
<213> ORGANISM: Staphylothermus marinus F1

<400> SEQUENCE: 20

```
Met Leu Arg Ile Ile Leu Ile Gly Pro Pro Gly Ala Gly Lys Gly Thr
 1               5                  10                  15

Tyr Ala Arg Tyr Phe Ser Lys Lys Tyr Cys Ile Pro His Ile Ser Thr
            20                  25                  30

Gly Asp Ile Phe Arg Glu Glu Val Ala Lys Gly Thr Glu Leu Gly Lys
        35                  40                  45

Lys Ile Lys Asp Ile Leu Asp Arg Gly Glu Leu Val Pro Asp Asp Ile
    50                  55                  60

Val Ile Glu Ile Val Lys Lys Arg Leu Gln Gln Pro Asp Thr Ala Lys
65                  70                  75                  80

Gly Phe Ile Leu Asp Gly Phe Pro Arg Thr Ile Arg Gln Ala Glu Ala
                85                  90                  95

Leu Asp Glu Ile Thr Lys Leu Asp Ala Ala Ile His Ile Tyr Ile Ala
            100                 105                 110

Met Glu Glu Ala Val Arg Arg Leu Ser Asn Arg Tyr Ile Cys Pro Lys
        115                 120                 125

Cys Gly Arg Val Tyr Asn Leu Leu Phe Asn Pro Pro Lys Asn Asp Leu
    130                 135                 140

Arg Cys Asp Asp Asp Gly Thr Pro Leu Ile Arg Arg Ser Asp Asp Glu
145                 150                 155                 160

Pro Glu Val Ile Arg Arg Tyr Lys Ile Tyr Glu Thr Phe Gln
                165                 170                 175

Pro Ile Ile Glu Tyr Tyr Lys Lys Asn Leu Leu Ile Glu Ile Asp
            180                 185                 190

Asn Thr Ile Gly Ser Asp Lys Gly Ile Pro Leu Leu Glu Lys Ile Leu
        195                 200                 205

Ile Asp Lys Gly Ile Leu Lys Ile Glu Pro Cys Asn Pro Asn Val Ser
    210                 215                 220

Ile Lys
225
```

<210> SEQ ID NO 21
<211> LENGTH: 217
<212> TYPE: PRT
<213> ORGANISM: Thermoanaerobacter italicus Ab9

<400> SEQUENCE: 21

```
Met Lys Ile Ile Leu Leu Gly Pro Pro Gly Ala Gly Lys Gly Thr Gln
 1               5                  10                  15

Ala Val Lys Ile Ala Lys Glu Phe Asp Ile Pro His Ile Ser Thr Gly
            20                  25                  30

Asp Ile Phe Arg Gln Asn Leu Arg Glu Asn Thr Asp Leu Gly Lys Leu
        35                  40                  45

Ala Lys Glu Tyr Met Asp Lys Gly Leu Leu Val Pro Asp Glu Val Thr
    50                  55                  60

Asn Lys Ile Val Glu Asn Arg Leu Glu Lys Asn Asp Cys Gln Lys Gly
65                  70                  75                  80

Phe Leu Leu Asp Gly Tyr Pro Arg Asn Val Glu Gln Ala Glu Glu Leu
                85                  90                  95

Asp Arg Phe Leu Gln Gly Lys Gly Ile His Leu Asp Cys Val Leu Asn
            100                 105                 110

Ile Glu Val Glu Lys Glu Ala Leu Ile Glu Arg Ile Thr Gly Arg Arg
        115                 120                 125

Val Cys Pro Asn Cys Gly Ala Thr Tyr His Ile Lys Thr Phe Pro Pro
```

-continued

```
                130                 135                 140
Ala Val Asp Asn Val Cys Asp Lys Cys Gly Ala Gln Leu Ile Gln Arg
145                 150                 155                 160

Ser Asp Asp Lys Leu Glu Ser Ile Val Lys Arg Leu Glu Val Tyr Glu
                165                 170                 175

Ser Gln Thr Lys Pro Leu Ile Glu His Tyr Thr Lys Lys Gly Ile Leu
                180                 185                 190

Val Asn Ile Asp Gly Asn Lys Ser Val Glu Glu Val Phe Glu Asp Ile
                195                 200                 205

Lys Lys Val Leu Gly Asp Arg Gly Lys
210                 215
```

<210> SEQ ID NO 22
<211> LENGTH: 214
<212> TYPE: PRT
<213> ORGANISM: Ammonifex degensii KC4

<400> SEQUENCE: 22

```
Met Asn Leu Leu Ile Met Gly Pro Pro Gly Ala Gly Lys Gly Thr Gln
1               5                   10                  15

Ser Glu Arg Leu Val Lys Glu Phe Asn Ile Pro His Ile Ser Thr Gly
                20                  25                  30

Asp Met Leu Arg Glu Ala Val Lys Gln Gly Thr Glu Met Gly Lys Lys
            35                  40                  45

Ala Lys Glu Tyr Met Asp Lys Gly Gln Leu Val Pro Asp Glu Val Ile
        50                  55                  60

Ile Gly Val Val Lys Glu Arg Leu Met Gln Pro Asp Cys Glu Arg Gly
65              70                  75                  80

Phe Leu Leu Asp Gly Phe Pro Arg Thr Val Ala Gln Ala Glu Ala Leu
                85                  90                  95

Asp Lys Leu Leu Leu Glu Met Gly Arg Lys Leu Asp Ala Val Ile Asn
            100                 105                 110

Val Ser Val Pro Arg Glu Lys Ile Val Ala Arg Leu Thr Gly Arg Arg
        115                 120                 125

Val Cys Lys Val Cys Gly Ala Thr Tyr His Ile Val Asn Asn Pro Pro
130                 135                 140

Lys Val Glu Gly Lys Cys Asp Lys Cys Gly Gly Glu Leu Tyr Gln Arg
145                 150                 155                 160

Ser Asp Asp Thr Glu Glu Thr Val Asn Lys Arg Leu Asp Val Tyr Glu
                165                 170                 175

Ala Gln Thr Gln Pro Leu Ile Glu Tyr Tyr Gln Ala Lys Gly Leu Leu
                180                 185                 190

Val Asn Ile Asp Gly Asp Gln Pro Ile Asp Lys Val Phe Ala Asp Ile
                195                 200                 205

Met Ala Ala Leu Lys Lys
210
```

<210> SEQ ID NO 23
<211> LENGTH: 219
<212> TYPE: PRT
<213> ORGANISM: Thermotogales bacterium mesG1.Ag.4.2

<400> SEQUENCE: 23

```
Met Asn Val Ile Leu Met Gly Pro Pro Gly Ala Gly Lys Gly Thr Gln
1               5                   10                  15

Ala Lys Arg Ile Ala Gln Ile Phe Lys Ile Pro His Ile Ser Thr Gly
                20                  25                  30
```

```
Asp Met Leu Arg Glu Ala Val Ala Ala Gly Thr Asp Leu Gly Leu Lys
        35                  40                  45

Val Lys Glu Ile Met Asp Lys Gly Leu Leu Val Pro Asp Asp Leu Met
 50                  55                  60

Ile Asp Leu Val Arg Glu Arg Leu Ser Arg Glu Asp Thr Arg Asn Gly
 65                  70                  75                  80

Phe Ile Leu Asp Gly Phe Pro Arg Thr Val Glu Gln Ala Ala Ala Leu
                 85                  90                  95

Asp Glu Met Leu Glu Asp Leu Gly Arg Lys Ile Asp Val Ala Leu Leu
            100                 105                 110

Val Asn Ala Asp Glu Glu Val Val Lys Arg Ile Ser Ser Arg Arg
            115                 120                 125

Val Cys Pro Glu Cys Gly Lys Val Tyr Asn Leu Leu Thr Ile Arg Pro
            130                 135                 140

Lys Val Glu Gly Arg Cys Asp Asn Asp Gly Ala Glu Leu Ile Gln Arg
145                 150                 155                 160

Asp Asp Asp Met Pro Glu Thr Val Arg Ala Arg Tyr Arg Val Tyr Leu
                165                 170                 175

Glu Lys Thr Glu Pro Val Ile Gln Tyr Tyr Ser Ser Asn Lys Ser Gln
            180                 185                 190

Phe Leu Glu Val Asp Gly Thr Gly Glu Ile Asp Val Val Thr Asp Lys
            195                 200                 205

Ile Val Glu His Leu Glu Ser Thr Arg Asn Gly
            210                 215

<210> SEQ ID NO 24
<211> LENGTH: 217
<212> TYPE: PRT
<213> ORGANISM: Thermoanaerobacter wiegelii Rt8.B1

<400> SEQUENCE: 24

Met Arg Val Ile Leu Leu Gly Pro Pro Gly Ala Gly Lys Gly Thr Gln
 1               5                  10                  15

Ala Val Lys Ile Ala Lys Glu Phe Asp Ile Pro His Ile Ser Thr Gly
             20                  25                  30

Asp Ile Phe Arg Gln Asn Leu Arg Asp Asn Thr Asp Leu Gly Lys Leu
         35                  40                  45

Ala Lys Glu Tyr Met Asp Lys Gly Leu Leu Val Pro Asp Glu Val Thr
 50                  55                  60

Asn Lys Ile Val Glu Asp Arg Leu Lys Asp Cys Gln Lys Gly
 65                  70                  75                  80

Phe Leu Leu Asp Gly Tyr Pro Arg Asn Val Thr Gln Ala Glu Glu Leu
                 85                  90                  95

Asp Arg Phe Leu Gln Gln Lys Gly Thr Tyr Leu Asp Cys Val Leu Asn
            100                 105                 110

Ile Lys Val Glu Lys Asp Ala Leu Ile Glu Arg Ile Thr Gly Arg Arg
            115                 120                 125

Val Cys Pro Asn Cys Gly Ala Thr Tyr His Ile Lys Thr Ser Pro Pro
            130                 135                 140

Ala Val Asp Asn Val Cys Asp Lys Cys Ser Thr Lys Leu Ile Gln Arg
145                 150                 155                 160

Ser Asp Asp Lys Leu Glu Ser Val Val Lys Arg Leu Glu Val Tyr Glu
                165                 170                 175

Ser Gln Thr Lys Pro Leu Ile Glu Tyr Tyr Thr Lys Lys Asn Ile Leu
            180                 185                 190
```

```
Val Asn Ile Asp Gly Asn Lys Ser Val Glu Glu Val Phe Glu Asp Ile
        195                 200                 205

Lys Lys Ala Leu Gly Asp Arg Gly Lys
    210                 215
```

<210> SEQ ID NO 25
<211> LENGTH: 214
<212> TYPE: PRT
<213> ORGANISM: Thermincola sp. JR

<400> SEQUENCE: 25

```
Met Lys Leu Met Ile Met Gly Pro Pro Gly Ala Gly Lys Gly Thr Gln
1               5                   10                  15

Ala Glu Val Leu Val Lys Glu Leu Asn Ile Thr His Ile Ser Thr Gly
            20                  25                  30

Asp Met Phe Arg Ala Ala Ile Lys Glu Gly Thr Glu Met Gly Lys Lys
        35                  40                  45

Ala Lys Glu Tyr Met Asp Lys Gly Gln Leu Val Pro Asp Glu Val Val
    50                  55                  60

Val Gly Met Val Lys Asp Arg Leu Ser Gln Pro Asp Cys Glu Lys Gly
65                  70                  75                  80

Phe Leu Leu Asp Gly Phe Pro Arg Thr Ile Ala Gln Ala Glu Ala Leu
                85                  90                  95

Ser Lys Thr Leu Asp Glu Met Gly Ile Lys Leu Asp Gly Val Ile Asn
            100                 105                 110

Ile Glu Val Pro Arg Glu Lys Leu Leu Ala Arg Leu Thr Gly Arg Arg
        115                 120                 125

Val Cys Lys Ser Cys Gly Ala Ser Tyr His Val Leu Phe Asn Pro Pro
    130                 135                 140

Glu Lys Glu Gly Val Cys Asn Asn Cys Gly Gly Glu Leu Tyr Gln Arg
145                 150                 155                 160

Ser Asp Asp Asn Glu Glu Thr Val Asn Asn Arg Leu Asp Val Tyr Glu
                165                 170                 175

Glu Gln Thr Gln Pro Leu Ile Asp Tyr Tyr Lys Glu Lys Gly Leu Leu
            180                 185                 190

Ile Asn Ile Asn Gly Asp Gln Pro Ile Asp Lys Val Leu Ala Asp Ile
        195                 200                 205

Leu Ala Ala Leu Arg Lys
    210
```

<210> SEQ ID NO 26
<211> LENGTH: 226
<212> TYPE: PRT
<213> ORGANISM: Staphylothermus hellenicus DSM 12710

<400> SEQUENCE: 26

```
Met Leu Arg Ile Val Leu Ile Gly Pro Pro Gly Ala Gly Lys Gly Thr
1               5                   10                  15

Tyr Ala Arg Tyr Phe Ser Lys Lys Tyr Cys Ile Pro His Ile Ser Thr
            20                  25                  30

Gly Asp Ile Phe Arg Glu Glu Val Ala Lys Gly Thr Glu Leu Gly Lys
        35                  40                  45

Arg Ile Lys Asp Ile Leu Asp Arg Gly Glu Leu Val Pro Asp Glu Ile
    50                  55                  60

Val Ile Glu Ile Val Arg Lys Arg Leu Arg Gln Pro Asp Thr Ala Lys
65                  70                  75                  80
```

```
Gly Phe Ile Leu Asp Gly Phe Pro Arg Thr Ile Arg Gln Ala Glu Ala
                85                  90                  95

Leu Asp Glu Ile Ala Thr Leu Asp Ala Val Ile His Ile Tyr Ile Thr
            100                 105                 110

Met Glu Glu Ala Val Arg Arg Leu Ser Asn Arg Tyr Ile Cys Pro Lys
        115                 120                 125

Cys Gly Arg Val Tyr Asn Leu Leu Phe Asn Pro Pro Lys Asn Asp Leu
    130                 135                 140

Arg Cys Asp Asp Asp Gly Thr Pro Leu Ile Arg Arg Ser Asp Asp Glu
145                 150                 155                 160

Pro Glu Val Ile Arg Arg Tyr Lys Ile Tyr Glu Thr Phe Gln
                165                 170                 175

Pro Ile Ile Glu Tyr Tyr Lys Lys Asn Leu Leu Ile Glu Ile Asp
            180                 185                 190

Asn Thr Ile Gly Ser Asp Lys Gly Ile Pro Leu Leu Glu Arg Thr Leu
            195                 200                 205

Ile Asp Lys Gly Ile Leu Lys Leu Lys Pro Cys Asn Pro Asn Val Ser
210                 215                 220

Ile Lys
225

<210> SEQ ID NO 27
<211> LENGTH: 217
<212> TYPE: PRT
<213> ORGANISM: Clostridium thermocellum ATCC 27405

<400> SEQUENCE: 27

Met Arg Leu Val Leu Leu Gly Ala Pro Gly Ala Gly Lys Gly Thr Gln
1               5                   10                  15

Ala Val Val Ile Ser Gln Lys Tyr Asn Val Pro His Ile Ser Thr Gly
            20                  25                  30

Asp Ile Phe Arg Ser Asn Ile Lys Asn Gly Thr Glu Leu Gly Arg Lys
        35                  40                  45

Ala Lys Glu Tyr Ile Asp Lys Gly Leu Leu Val Pro Asp Glu Leu Thr
    50                  55                  60

Val Asp Ile Val Lys Asp Arg Ile Ser Gln Pro Asp Cys Lys Ala Gly
65                  70                  75                  80

Phe Ile Leu Asp Gly Phe Pro Arg Thr Ile Tyr Gln Ala Glu Arg Leu
                85                  90                  95

Asp Glu Ile Leu Lys Glu Leu Asn Val Glu Leu Asp Cys Ala Leu Asn
            100                 105                 110

Ile Tyr Val Pro Asp Glu Glu Ile Ile Lys Arg Met Ser Gly Arg Arg
        115                 120                 125

Val Cys Ser Lys Cys Gly Met Ser Tyr His Ile Val Tyr Asn Gln Pro
    130                 135                 140

Lys Val Glu Asn Ile Cys Asp Ser Cys Asn Gly Glu Leu Ile Gln Arg
145                 150                 155                 160

Asp Asp Asp Lys Glu Glu Thr Val Ile Gln Arg Leu Asn Thr Tyr His
                165                 170                 175

Lys Gln Thr Glu Pro Leu Ile Glu Tyr Tyr Glu Lys Lys Gly Lys Leu
            180                 185                 190

Leu Thr Val His Gly Gln Glu Gly Val Asp Asp Thr Thr Lys Glu Val
        195                 200                 205

Leu Asn Ala Leu Ser Gly Val Lys Leu
    210                 215
```

<210> SEQ ID NO 28
<211> LENGTH: 211
<212> TYPE: PRT
<213> ORGANISM: Thermanaerovibrio acidaminovorans DSM 6589

<400> SEQUENCE: 28

Met Arg Val Ile Leu Leu Gly Pro Gly Ala Gly Lys Gly Thr Gln
1               5                   10                  15

Ala Ala Ala Val Lys Glu Arg Tyr Arg Ile Pro His Ile Ser Thr Gly
            20                  25                  30

Asp Met Leu Arg Glu His Val Lys Gly Gly Thr Glu Leu Gly Arg Lys
        35                  40                  45

Ala Lys Glu Phe Met Asp Gly Gly Lys Leu Val Pro Asp Gln Leu Ile
    50                  55                  60

Ile Ala Met Met Glu Asp Arg Leu Ser Gln Gly Asp Cys Glu Asn Gly
65                  70                  75                  80

Phe Leu Leu Asp Gly Phe Pro Arg Thr Val Pro Gln Ala Glu Ala Leu
                85                  90                  95

Asp Glu Leu Leu Ser Arg Met Gly Leu Gln Leu Asp Ala Val Val Leu
            100                 105                 110

Leu Glu Val Ala Asp Glu Val Val Gln Arg Leu Ser Gly Arg Arg
        115                 120                 125

Val Cys Arg Ser Cys Gly Ala Ile Tyr His Val Ser Phe His Pro Ser
    130                 135                 140

Ser Lys Gly Asp Leu Cys Glu Ala Cys Gly Gly Asp Leu Tyr Gln Arg
145                 150                 155                 160

Asp Asp Asp Arg Glu Asp Val Ile Arg Arg Leu Ser Val Tyr His
                165                 170                 175

Glu Gln Thr Ser Pro Leu Glu Ala Tyr Tyr Asp Ala Lys Gly Leu Leu
            180                 185                 190

Arg Arg Val Asn Gly Gly Ala Thr Asp Ala Val Leu Arg Cys Leu
        195                 200                 205

Glu Gly Leu
    210

<210> SEQ ID NO 29
<211> LENGTH: 215
<212> TYPE: PRT
<213> ORGANISM: Caldicellulosiruptor saccharolyticus

<400> SEQUENCE: 29

Met Arg Leu Ile Ile Leu Gly Ala Pro Gly Ala Gly Lys Gly Thr Gln
1               5                   10                  15

Ala Glu Tyr Leu Ser Ser Arg Phe Gly Ile Pro His Ile Ser Thr Gly
            20                  25                  30

Asp Ile Leu Arg Glu Asn Val Lys Asn Gln Thr Glu Leu Gly Lys Lys
        35                  40                  45

Ala Lys Glu Tyr Met Asp Lys Gly Leu Leu Val Pro Asp Glu Ile Val
    50                  55                  60

Ile Glu Ile Val Lys Asn Arg Leu Met Gln Asp Asp Cys Lys Asn Gly
65                  70                  75                  80

Phe Leu Leu Asp Gly Phe Pro Arg Thr Ile Ala Gln Ala Glu Ala Leu
                85                  90                  95

Glu Lys Val Leu Ala Asp Leu Gly Gln Lys Ile Asp Lys Val Leu Asn
            100                 105                 110

Ile Glu Val Pro Asp Glu Lys Ile Leu Glu Arg Met Ser Gly Arg Arg

```
                    115                 120                 125
Ile Cys Lys Ser Cys Gly Ala Ser Phe His Val Val Tyr Arg Pro Pro
    130                 135                 140

Lys Lys Glu Gly Ile Cys Asp Ile Cys Gly Gly Gln Leu Tyr Gln Arg
145                 150                 155                 160

Glu Asp Asp Lys Glu Thr Val Lys Lys Arg Leu Glu Val Tyr His
                    165                 170                 175

Ala Gln Thr Gln Pro Leu Ile Glu Tyr Tyr Lys Asn Lys Gly Leu Leu
                180                 185                 190

Val Thr Ala Val Gly Gln Glu Glu Ile Ala Asp Thr Thr Lys Glu Val
                195                 200                 205

Leu Lys Ala Leu Gly Val Glu
    210                 215

<210> SEQ ID NO 30
<211> LENGTH: 217
<212> TYPE: PRT
<213> ORGANISM: Clostridium thermocellum JW20

<400> SEQUENCE: 30

Met Arg Leu Val Leu Leu Gly Ala Pro Gly Ala Gly Lys Gly Thr Gln
1               5                   10                  15

Ala Val Val Ile Ser Gln Lys Tyr Asn Val Pro His Ile Ser Thr Gly
                20                  25                  30

Asp Ile Phe Arg Ser Asn Ile Lys Asn Gly Thr Glu Leu Gly Arg Lys
            35                  40                  45

Ala Lys Glu Tyr Ile Asp Lys Gly Leu Leu Val Pro Asp Glu Leu Thr
50                  55                  60

Val Asp Ile Val Lys Asp Arg Ile Ser Gln Pro Asp Cys Lys Ala Gly
65                  70                  75                  80

Phe Ile Leu Asp Gly Phe Pro Arg Thr Ile Tyr Gln Ala Glu Arg Leu
                85                  90                  95

Asp Glu Ile Leu Lys Glu Leu Asn Val Glu Leu Asp Cys Thr Leu Asn
            100                 105                 110

Ile Tyr Val Pro Asp Glu Glu Ile Ile Lys Arg Met Ser Gly Arg Arg
        115                 120                 125

Val Cys Ser Lys Cys Gly Met Ser Tyr His Ile Val Tyr Asn Gln Pro
    130                 135                 140

Lys Val Glu Asn Ile Cys Asp Ser Cys Asn Gly Glu Leu Ile Gln Arg
145                 150                 155                 160

Asp Asp Asp Lys Glu Glu Thr Val Ile Gln Arg Leu Asn Thr Tyr His
                165                 170                 175

Lys Gln Thr Glu Pro Leu Ile Glu Tyr Tyr Glu Lys Lys Gly Lys Leu
                180                 185                 190

Leu Thr Val His Gly Gln Glu Gly Val Asp Asp Thr Thr Lys Glu Val
                195                 200                 205

Leu Asn Ala Leu Ser Gly Val Lys Leu
    210                 215

<210> SEQ ID NO 31
<211> LENGTH: 213
<212> TYPE: PRT
<213> ORGANISM: Geobacillus stearothermophilus

<400> SEQUENCE: 31

Met Asn Leu Val Leu Met Gly Leu Pro Gly Ala Gly Lys Gly Thr Gln
1               5                   10                  15
```

```
Ala Glu Lys Ile Val Glu Thr Tyr Gly Ile Pro His Ile Ser Thr Gly
            20                  25                  30

Asp Met Phe Arg Ala Ala Ile Lys Glu Gly Thr Pro Leu Gly Leu Gln
        35                  40                  45

Ala Lys Glu Tyr Met Asp Arg Gly Asp Leu Val Pro Asp Glu Val Thr
    50                  55                  60

Ile Gly Ile Val Arg Glu Arg Leu Ser Lys Asp Asp Cys Gln Lys Gly
65                  70                  75                  80

Phe Leu Leu Asp Gly Phe Pro Arg Thr Val Ala Gln Ala Glu Ala Leu
                85                  90                  95

Glu Asn Ile Leu Ala Glu Leu Asn Arg Ser Ile Asp Tyr Val Ile His
            100                 105                 110

Ile His Val Asp Lys Asp Ile Leu Met Glu Arg Leu Thr Gly Arg Arg
            115                 120                 125

Ile Cys Lys Asn Cys Gly Ala Thr Tyr His Leu Val Phe Asn Pro Pro
130                 135                 140

Ala Lys Pro Gly Val Cys Asp Lys Cys Gly Gly Glu Leu Tyr Gln Arg
145                 150                 155                 160

Ala Asp Asp Asn Glu Glu Thr Val Ala Asn Arg Leu Glu Val Asn Val
                165                 170                 175

Lys Gln Thr Gln Pro Leu Leu Asp Phe Tyr Glu Lys Lys Gly Tyr Leu
            180                 185                 190

Arg His Ile Asn Gly Gln Gln Asp Ile Glu Lys Val Phe Ala Asp Ile
            195                 200                 205

Arg Glu Leu Leu Gly
        210

<210> SEQ ID NO 32
<211> LENGTH: 12
<212> TYPE: PRT
<213> ORGANISM: Artificial Sequence
<220> FEATURE:
<223> OTHER INFORMATION: Synthetic peptide

<400> SEQUENCE: 32

Gly Ala Ser Gly Gly Gly Ser Ser Gly Gly His Met
1               5                   10
```